US009492574B2

(12) United States Patent
Rasooly et al.

(10) Patent No.: US 9,492,574 B2
(45) Date of Patent: Nov. 15, 2016

(54) APPARATUS FOR DISINFECTING OR STERILIZING A CATHETER AND METHOD OF USE

(71) Applicant: PuraCath Medical, Inc., Mountain View, CA (US)

(72) Inventors: Julia A. Rasooly, San Francisco, CA (US); Mark Juravic, San Franciso, CA (US); Mitchell C. Barham, San Mateo, CA (US)

(73) Assignee: PuraCath Medical, Inc., San Francisco, CA (US)

( * ) Notice: Subject to any disclaimer, the term of this patent is extended or adjusted under 35 U.S.C. 154(b) by 0 days.

(21) Appl. No.: 14/166,291

(22) Filed: Jan. 28, 2014

(65) Prior Publication Data

US 2014/0334974 A1    Nov. 13, 2014

Related U.S. Application Data

(60) Provisional application No. 61/757,999, filed on Jan. 29, 2013.

(51) Int. Cl.
| | | |
|---|---|---|
| *A61L 2/10* | (2006.01) | |
| *A61M 39/16* | (2006.01) | |
| *A61M 1/28* | (2006.01) | |
| *A61M 1/36* | (2006.01) | |

(52) U.S. Cl.
CPC .................. *A61L 2/10* (2013.01); *A61M 1/285* (2013.01); *A61M 1/3659* (2014.02); *A61M 39/16* (2013.01)

(58) Field of Classification Search
CPC ....................................................... A61L 2/10

USPC .......................................................... 422/24
See application file for complete search history.

(56) References Cited

U.S. PATENT DOCUMENTS

| | | | |
|---|---|---|---|
| 3,517,669 | A | 6/1970 | Buono et al. |
| 3,572,375 | A | 3/1971 | Rosenberg |
| 3,626,938 | A | 12/1971 | Versaci |
| 3,986,508 | A | 10/1976 | Barrington |
| 4,209,013 | A | 6/1980 | Alexander et al. |
| 4,232,428 | A | 11/1980 | Johansson |
| 4,242,310 | A | 12/1980 | Greff et al. |
| 4,256,135 | A | 3/1981 | Hannah |

(Continued)

FOREIGN PATENT DOCUMENTS

| | | |
|---|---|---|
| EP | 0229786 B1 | 3/1990 |
| EP | 0163811 B1 | 8/1991 |

(Continued)

OTHER PUBLICATIONS

Bak et al.; Disinfection of pseudomonas aeruginosa biofilm contaminated tube lumens with ultraviolet C light emitting diodes; Biofouling: The Journal of Bioadhesion and Biofilm Research; 26(1); pp. 31-38; Jan. 2010.

(Continued)

*Primary Examiner* — Kevin Joyner
*Assistant Examiner* — Holly Mull
(74) *Attorney, Agent, or Firm* — Shay Glenn LLP

(57) ABSTRACT

An elliptical-shaped housing contains a UV light source and a power source. A connector is removably mounted in the housing and is disinfected or sterilized by UV light. A reflective coating inside the housing enhances the intensity of the UV light to disinfect or sterilize the connector.

10 Claims, 24 Drawing Sheets

(56) References Cited

U.S. PATENT DOCUMENTS

| | | | |
|---|---|---|---|
| 4,336,223 A | 6/1982 | Hillman | |
| 4,340,052 A | 7/1982 | Dennehey et al. | |
| 4,346,704 A | 8/1982 | Kulle | |
| 4,412,834 A | 11/1983 | Kulin et al. | |
| 4,433,244 A | 2/1984 | Hogan | |
| 4,439,188 A | 3/1984 | Dennehey et al. | |
| 4,440,207 A | 4/1984 | Genatempo et al. | |
| 4,469,835 A | 9/1984 | Laurin | |
| 4,473,369 A | 9/1984 | Lueders et al. | |
| 4,475,900 A | 10/1984 | Popovich et al. | |
| 4,500,788 A | 2/1985 | Kulin et al. | |
| 4,541,829 A | 9/1985 | Munsch et al. | |
| 4,573,980 A | 3/1986 | Karrasch et al. | |
| 4,608,472 A | 8/1986 | Kato | |
| 4,620,845 A * | 11/1986 | Popovich et al. | 604/28 |
| 4,655,762 A | 4/1987 | Rogers | |
| 4,745,950 A | 5/1988 | Mathieu | |
| 4,774,415 A | 9/1988 | Biegel et al. | |
| 4,877,964 A | 10/1989 | Tanaka et al. | |
| 4,878,516 A | 11/1989 | Mathieu | |
| 4,882,496 A | 11/1989 | Bellotti et al. | |
| 4,948,980 A | 8/1990 | Wedekamp | |
| 4,949,723 A | 8/1990 | Wallace et al. | |
| 4,950,230 A | 8/1990 | Kendell | |
| 4,980,374 A | 12/1990 | Steudle et al. | |
| 5,047,011 A | 9/1991 | Caron et al. | |
| 5,057,074 A | 10/1991 | Suzuki et al. | |
| 5,105,853 A | 4/1992 | Lie | |
| 5,147,321 A | 9/1992 | Slonina et al. | |
| 5,190,534 A | 3/1993 | Kendell | |
| 5,221,267 A | 6/1993 | Folden | |
| 5,242,150 A | 9/1993 | Shiffler et al. | |
| 5,336,173 A | 8/1994 | Folden | |
| 5,417,673 A | 5/1995 | Gordon | |
| 5,427,135 A | 6/1995 | Kieper | |
| 5,536,258 A | 7/1996 | Folden | |
| 5,540,668 A | 7/1996 | Wilson et al. | |
| 5,603,902 A | 2/1997 | Maltais et al. | |
| 5,612,001 A | 3/1997 | Matschke | |
| 5,713,850 A | 2/1998 | Heilmann et al. | |
| 5,714,119 A | 2/1998 | Kawagoe et al. | |
| 5,855,203 A | 1/1999 | Matter | |
| 6,027,489 A | 2/2000 | Galato | |
| 6,120,166 A | 9/2000 | Price | |
| 6,228,332 B1 | 5/2001 | Dunn et al. | |
| 6,245,570 B1 | 6/2001 | Grimm et al. | |
| 6,418,257 B1 | 7/2002 | Nath | |
| 6,461,568 B1 | 10/2002 | Eckhardt | |
| 6,461,569 B1 | 10/2002 | Boudreaux | |
| 6,470,888 B1 | 10/2002 | Matter | |
| 6,485,483 B1 | 11/2002 | Fujii | |
| 6,569,564 B1 | 5/2003 | Lane | |
| 6,592,558 B2 | 7/2003 | Quah | |
| 6,682,507 B2 | 1/2004 | Irish | |
| 6,803,363 B2 | 10/2004 | Polaschegg | |
| 6,834,984 B2 | 12/2004 | Tausch et al. | |
| 7,083,605 B2 | 8/2006 | Miyahara | |
| 7,198,611 B2 | 4/2007 | Connell et al. | |
| 7,232,428 B1 | 6/2007 | Inukai et al. | |
| 7,232,429 B2 | 6/2007 | Moreci | |
| 7,274,847 B2 | 9/2007 | Gowda et al. | |
| 7,452,346 B2 | 11/2008 | Axelsson | |
| 7,497,849 B2 | 3/2009 | Fangrow | |
| 7,806,851 B2 | 10/2010 | Cerasoli | |
| 7,955,295 B2 | 6/2011 | Lee et al. | |
| 8,197,087 B2 | 6/2012 | Sobue et al. | |
| 8,282,829 B2 | 10/2012 | Yu et al. | |
| 8,431,074 B2 | 4/2013 | Neer | |
| 8,478,385 B2 | 7/2013 | Liu et al. | |
| 8,585,681 B2 | 11/2013 | Boenig et al. | |
| 8,641,659 B2 | 2/2014 | Soykan et al. | |
| 2003/0010927 A1 | 1/2003 | Wedekamp | |
| 2003/0017073 A1 | 1/2003 | Eckhardt et al. | |
| 2005/0013729 A1 | 1/2005 | Brown-Skrobot et al. | |
| 2005/0124970 A1 | 6/2005 | Kunin et al. | |
| 2005/0163655 A1 | 7/2005 | Lin et al. | |
| 2005/0261621 A1 | 11/2005 | Perez | |
| 2006/0027270 A1 | 2/2006 | Truitt et al. | |
| 2006/0122559 A1 | 6/2006 | Shia et al. | |
| 2006/0147339 A1 | 7/2006 | Hunter et al. | |
| 2006/0186010 A1 | 8/2006 | Warnack et al. | |
| 2007/0023710 A1 | 2/2007 | Tom et al. | |
| 2007/0176117 A1 | 8/2007 | Redmond et al. | |
| 2007/0179473 A1 | 8/2007 | Masters et al. | |
| 2007/0232989 A1 | 10/2007 | Kitani et al. | |
| 2007/0274879 A1 | 11/2007 | Millikin | |
| 2008/0045884 A1 | 2/2008 | Landherr et al. | |
| 2008/0183126 A1 | 7/2008 | Landherr et al. | |
| 2008/0183127 A1 | 7/2008 | Landherr et al. | |
| 2008/0195031 A1 | 8/2008 | Kitani et al. | |
| 2008/0306454 A1 | 12/2008 | Sikora | |
| 2009/0012451 A1 | 1/2009 | Sobue et al. | |
| 2009/0149776 A1 | 6/2009 | Adams | |
| 2009/0205664 A1 | 8/2009 | Lyon | |
| 2009/0257910 A1 | 10/2009 | Segal | |
| 2009/0259203 A1 | 10/2009 | Hu et al. | |
| 2009/0289015 A1 | 11/2009 | Levy | |
| 2009/0320316 A1 | 12/2009 | Zakai | |
| 2010/0072506 A1 | 3/2010 | Bae et al. | |
| 2010/0249586 A1 | 9/2010 | Cocker et al. | |
| 2011/0064608 A1 | 3/2011 | Lee et al. | |
| 2011/0085936 A1 | 4/2011 | Haytman et al. | |
| 2011/0165020 A1 | 7/2011 | Tryggvason et al. | |
| 2011/0213339 A1 | 9/2011 | Bak | |
| 2012/0053512 A1 | 3/2012 | Muse | |
| 2012/0161032 A1 | 6/2012 | Arcand et al. | |
| 2012/0205825 A1 | 8/2012 | Nagafuji et al. | |
| 2012/0206992 A1 | 8/2012 | Stewart | |
| 2012/0296151 A1 | 11/2012 | Curtis et al. | |
| 2012/0321509 A1 | 12/2012 | Bak | |
| 2013/0303996 A1 | 11/2013 | Rasooly et al. | |
| 2013/0323119 A1 | 12/2013 | Alwan | |
| 2014/0205498 A1 | 7/2014 | Bak | |

FOREIGN PATENT DOCUMENTS

| | | | |
|---|---|---|---|
| EP | 2161040 A1 | | 3/2010 |
| FR | 2799373 A1 | * | 4/2001 |
| JP | 2008/68049 | | 3/2008 |
| WO | WO92/19284 A1 | | 11/1992 |
| WO | WO2007/103998 A2 | | 9/2007 |
| WO | WO2008/014437 A2 | | 1/2008 |
| WO | WO2009/094034 A1 | | 7/2009 |
| WO | WO2011/000787 A1 | | 1/2011 |
| WO | WO2011/143140 A2 | | 11/2011 |

OTHER PUBLICATIONS

Bak et al.; Dose requirement for UVC disinfection of catheter biofilms; Biofouling: The Journal of Bioadhesion and Biofilm Research; 25(3); pp. 289-296; Apr. 2009.

Bak et al.; Potential in vivo UVC disinfection of catheter lumens: estimation of the doses received by the blood flow outside the catheter tip hole; Photochemistry and Photobiology; 87(2); pp. 350-356; Mar.-Apr. 2011.

Bak et al.; UVC fluencies of preventative treatment of pseudomonas aeruginosa contaminated polymer tubes; Biofouling: The Journal of Bioadhesion and Biofilm Research; 26(7); pp. 821-828; Oct. 2010.

Qamar et al; Clinical outcomes in peritoneal dialysis: Impact of continuous improvement quality initiatives; Advances in Peritoneal Dialysis; vol. 25; pp. 76-79; 2009 (year of pub. sufficiently earlier than effective US filing and any foreign priority date).

Murphy-Chutorian et al.; U.S. Appl. No. 14/731,110 entitled; "Transfer catheter for ultraviolet disinfection," filed Jun. 4, 2015.

Kermode et al.; U.S. Appl. No. 14/857,522 entitled "Ultraviolet disinfection unit," filed Sep. 17, 2015.

* cited by examiner

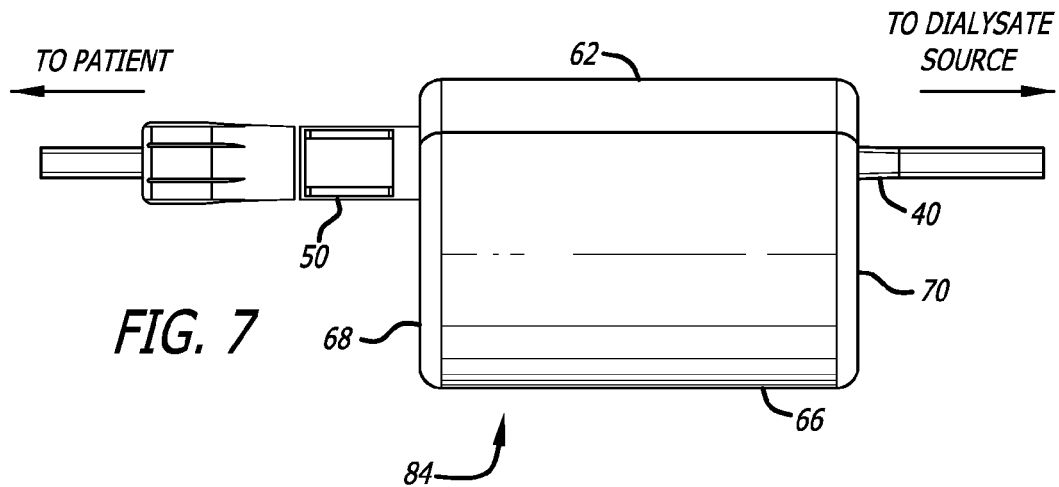
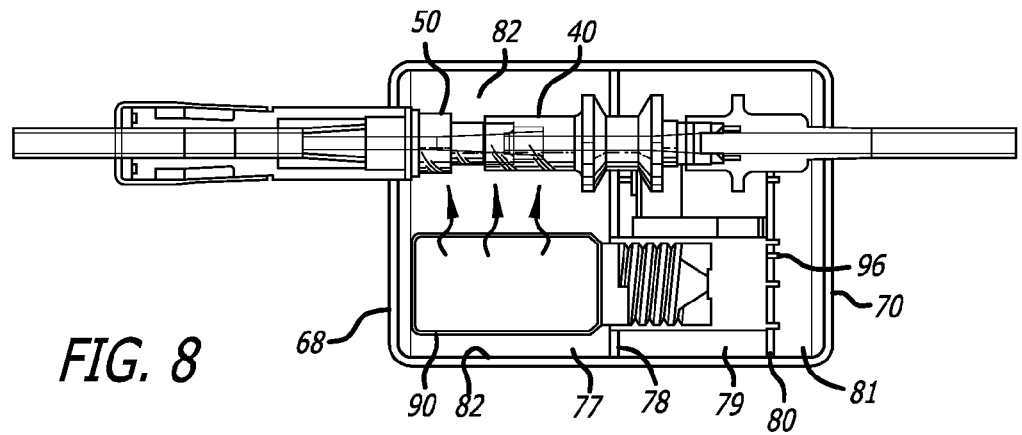

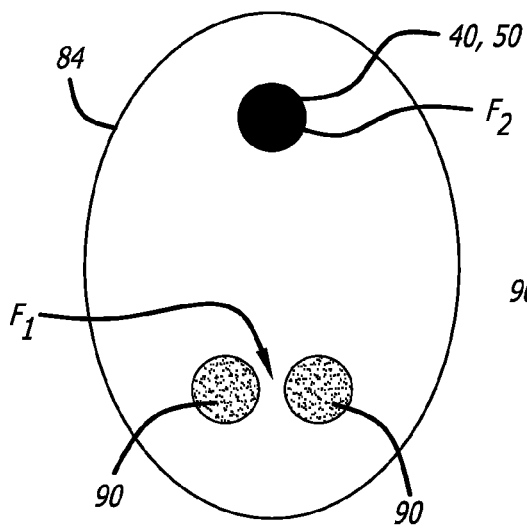
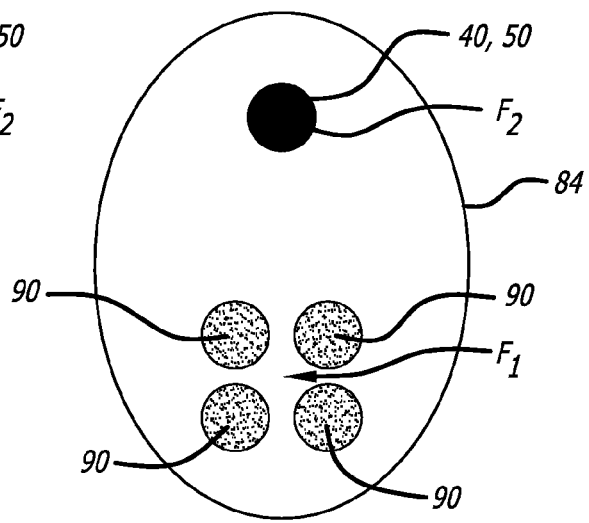
FIG. 14　　　　　　　FIG. 15
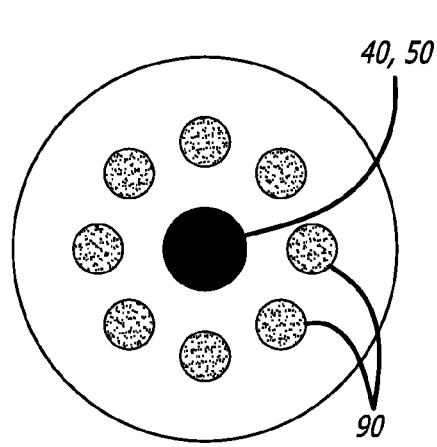
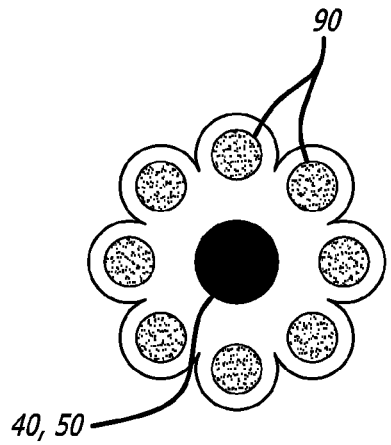
FIG. 16　　　　　　　FIG. 17

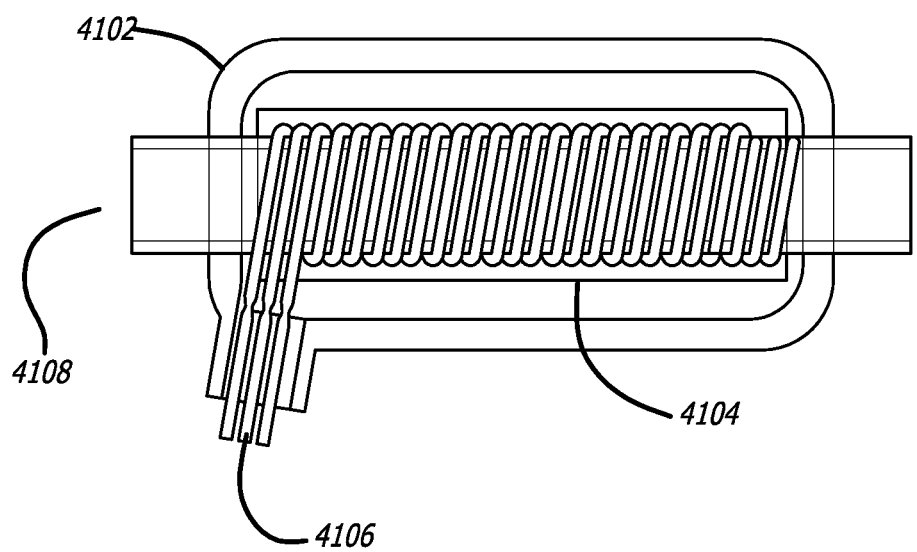
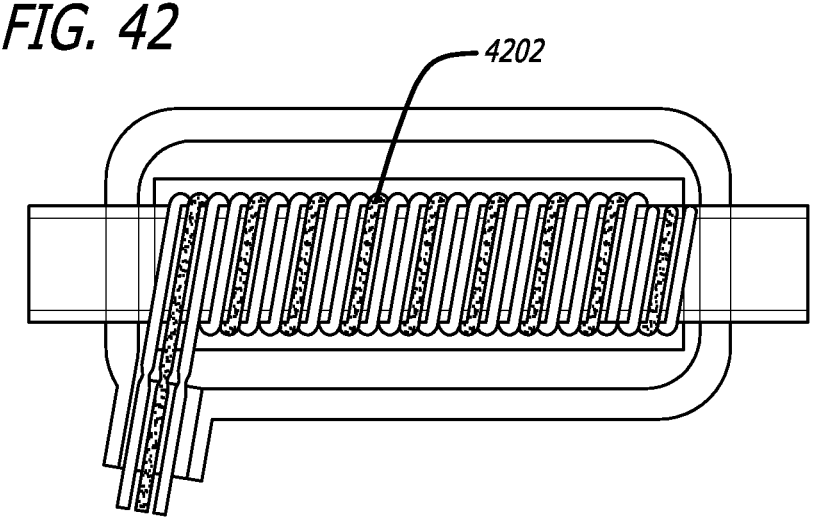

APPARATUS FOR DISINFECTING OR STERILIZING A CATHETER AND METHOD OF USE

CROSS-REFERENCES TO RELATED APPLICATIONS

This application claims priority to and the benefit of U.S. Provisional Application No. 61/757,999 filed Jan. 29, 2013, the entire disclosure of which is expressly incorporated by reference herein.

BACKGROUND

This application relates generally to the disinfection or sterilization of catheters, tubes, and connectors and more particularly to disinfection or sterilization of catheters, tubes and connectors used in dialysis, and more particularly, to peritoneal dialysis. Peritoneal dialysis (PD) is a treatment for chronic kidney disease (CKD), a condition in which the kidneys fail to remove waste and excess water from the bloodstream. In PD, a dialysis solution enters the abdomen through an access site. After a few hours, the fluid becomes saturated with waste and is eventually drained through a catheter. There are two types of PD. Under continuous ambulatory peritoneal dialysis (CAPD), patients change fluid four times a day. Continuous cycling peritoneal dialysis (CCPD), on the other hand, occurs at night through a machine that drains and refills the abdomen automatically. Unlike most hemodialysis (HD) patients, PD patients perform dialysis themselves. The protocol for sterilization procedures for PD patients involves multiple steps and is highly susceptible to imperfection and to bacterial contamination at every step. Peritonitis infection are the leading cause for a PD patient to transfer to HD. The incidence of peritonitis is 0.27 episodes/patient year for CAPD patients, and 1.48/patient year for CCPD patients. The main bacterium that causes this peritonitis is *Staphylococcus aureus*, which is part of the normal flora of the skin. Treatment for peritonitis includes long-term antibiotic treatment that causes multiple side effects and does not always eradicate the infection.

However, PD has several advantages over hemodialysis including mobility, fewer dietary restrictions, less cardiovascular stress and better blood pressure. Its disadvantages are peritonitis, increased risk of back pain, loss of protein, and lower survival rates than HD after diagnosis of cardiovascular disease.

Applicant of the subject application determines that new devices and methods for preventing or reducing infections in dialysis would be desirable.

SUMMARY OF THE INVENTION

In accordance with some embodiments, a device for use in dialysis includes an elongated tubular body having a first end, a second end, and a lumen extending between the first end and the second end, and a first UV source associated with the elongated tubular body, wherein the first UV source is configured to direct UV light for sterilizing at least a part of the elongated tubular body.

In accordance with other embodiments, a device for use in dialysis includes a transfer set having a first end, a second end, and a lumen between the first end and the second end, and a Y-set for detachably coupling to the transfer set, and a UV light source for disinfecting or sterilizing the transfer set and the Y-set.

In accordance with another embodiment, an assembly for disinfecting a connector includes a housing having an elliptical shape wherein the housing has an inner surface and an outer surface and a hinged cover. A UV light source is mounted inside the housing so that no portion of the UV light source contacts the housing inner surface A power source and an electronic circuit control electrical power to the UV light source. A reflective coating is place on at least a portion of the housing inner surface for enhancing the intensity of the UV light source to disinfect the connector. In one embodiment, the connector includes a transfer set connected to a Y-set, both connectors being formed from a material that is UV light transmissive. In this embodiment, the UV light source is mounted inside the elliptical housing at first foci $F_1$, and the transfer set and Y-set connectors are positioned inside the elliptical housing at the second foci, $F_2$. As a result, the intensity of the UV light source is maximized in order to disinfect or sterilize the transfer set and the Y-set connectors.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 7 is a side elevational view of the outer surface of the elliptical housing with the transfer set connector and the Y-set connector mounted in the housing.

FIG. 8 is a cross sectional side view depicting the transfer set connector and the Y-set connector mounted in the housing with the UV light source positioned below the connectors.

FIGS. 14 and 15 are schematic views depicting a connector positioned at one foci in an elliptical-shaped housing and multiple UV light sources positioned at the second foci.

FIGS. 16 and 17 are schematic views depicting a connector surrounded multiple light sources and a parabolic reflector.

FIGS. 41 and 42 are elevational views, partially in section, depicting fiber optic cables wrapped in coils in a dialysate chamber.

DESCRIPTION OF THE PREFERRED EMBODIMENTS

Figure 1:
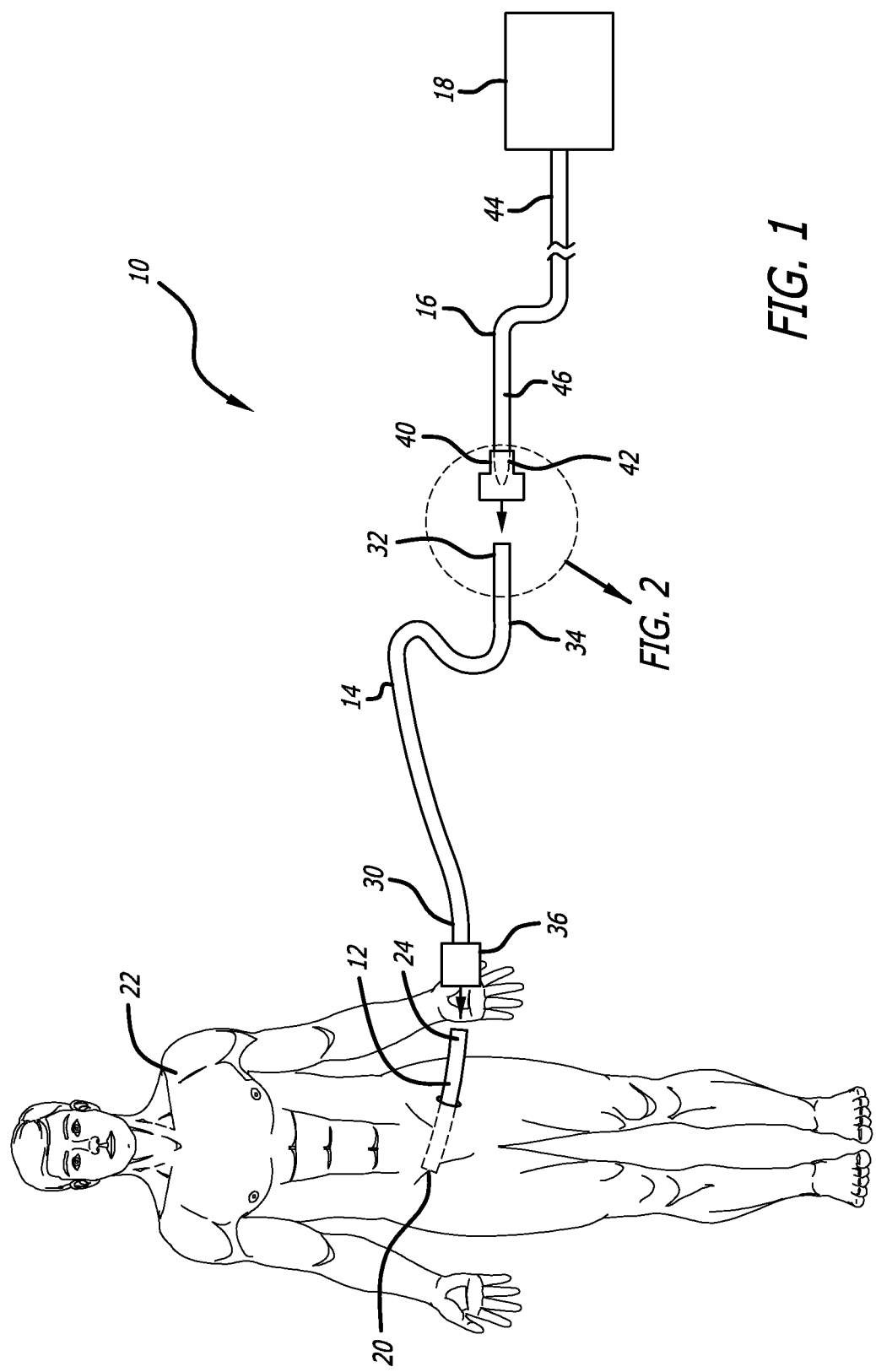
FIG. 1 illustrates a dialysis system for peritoneal dialysis in accordance with some embodiments, particularly showing the dialysis system having a tubular body and a catheter configured to detachably couple to an end of the tubular body.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

As used herein, to "disinfect" means to cleanse something so as to destroy or prevent the growth of disease-carrying microorganisms. *Stedman's Medical Dictionary*, 1995, p. 235. Further, use of the term "sterilize" means to make free from live bacteria or other microorganisms. Id. at p. 788.

FIG. 1 illustrates a peritoneal dialysis system 10 in accordance with some embodiments. The system 10 includes an implantable tube 12, an elongated tubular body 14, a catheter 16, and a dialysate bag 18. The implantable tube 12 includes a first end 20 for implant inside a patient 22, and a second end 24. The elongated tubular body 14 includes a first end 30 configured (e.g. sized and/or shaped) for detachably coupling to the second end 24 of the implantable tube 12 through a connector 36, a second end 32, and a lumen 34 between the first end 30 and second end 32. In some embodiments, the connector 36 may be considered to be a part of the elongated tubular body 14 (e.g., it may be considered to be a part of the first end 30). The catheter 16 includes a first end 42, a second end 44, and a lumen 46 between the first end 42 and the second end 44. The first end 42 of the catheter 16 is configured to detachably couple to the second end 32 of the elongated tubular body 14 through a transmissive Y-set connector 40. The second end 44 of the catheter 16 is configured to couple to the dialysate bag 18. The Y-set connector 40 may be considered to be a part of the system 10. In other embodiments, the Y-set connector 40 may be considered to be a part of the catheter 16 or a part of the elongated tubular body 14.

Figure 2:
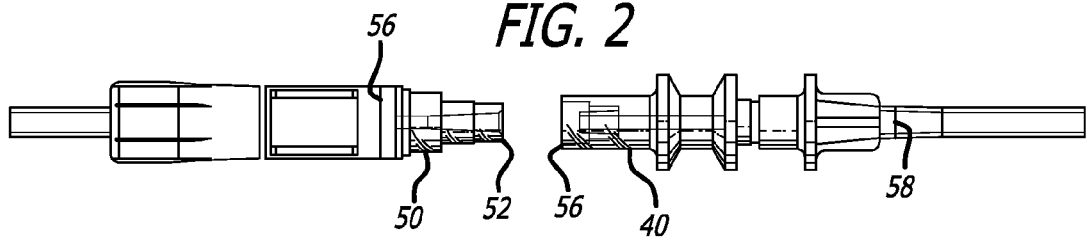
FIG. 2 is a side elevational view depicting a transfer set connector (on the left side of the drawing) and a Y-set connector (on the right side of the drawing).
Figure 3:
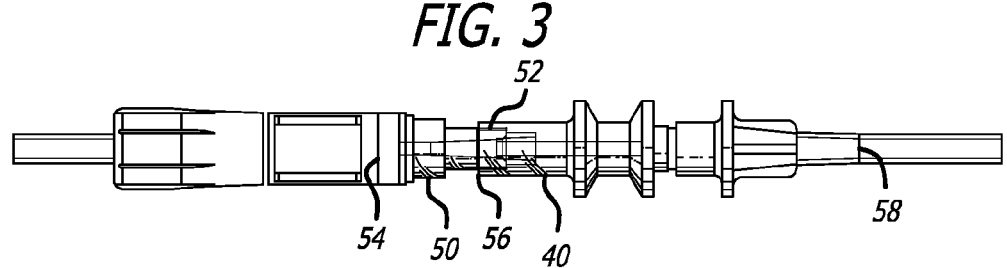
FIG. 3 is a side elevational view depicting the transfer set connector connected to the Y-set connector.
Figure 4:
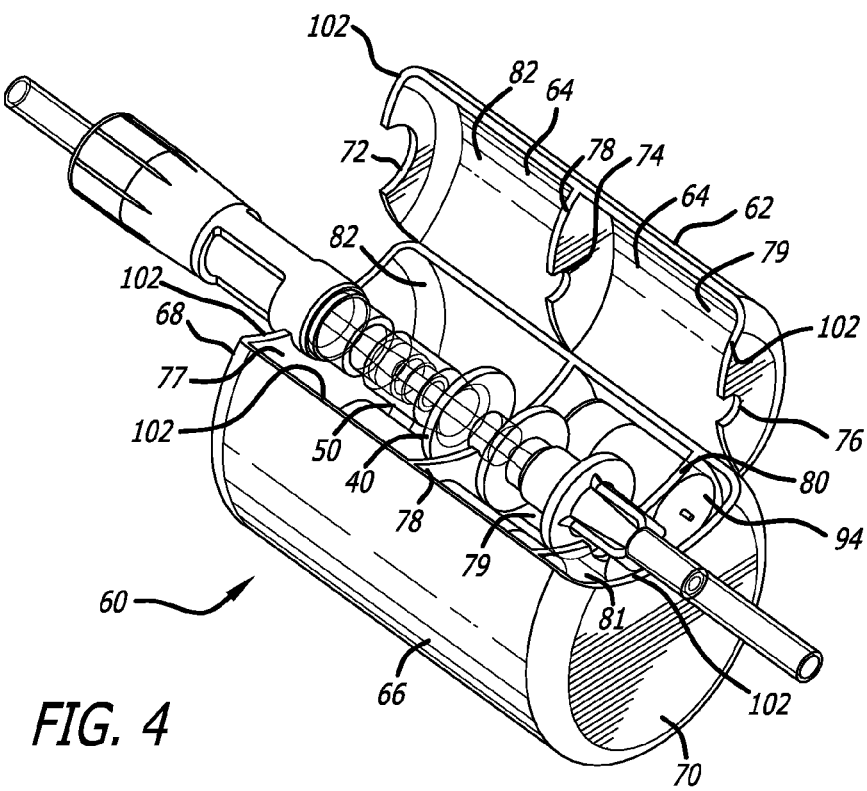
FIG. 4 is a perspective view depicting the elliptical-shaped housing with a hinged cover opened to show the transfer set connector connected to the Y-set connector and positioned inside the housing.
Figure 5:
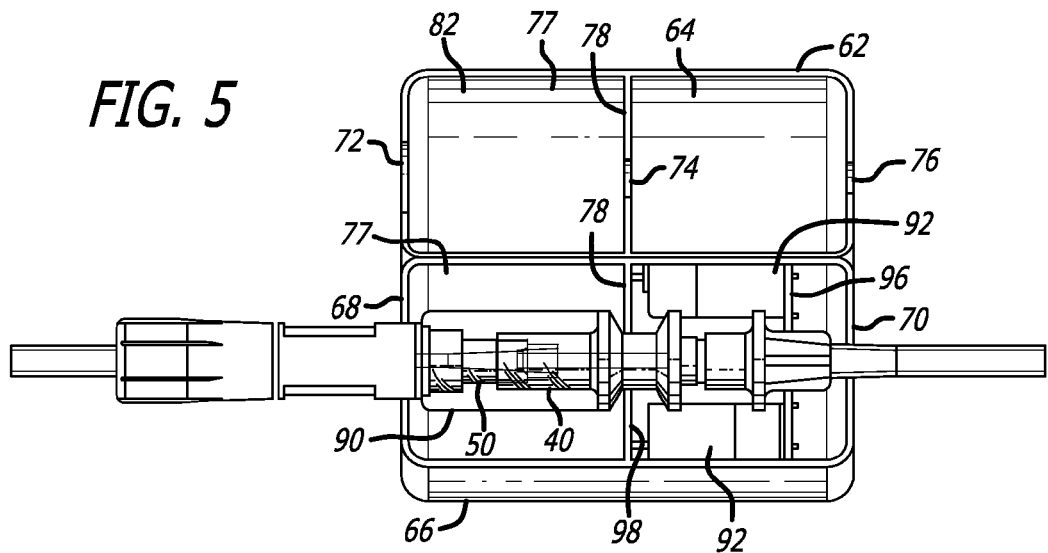
FIG. 5 is a top view of the elliptical-shaped housing with the hinged cover open and depicting the transfer set connector and the Y-set connector positioned inside the housing.
Figure 6:
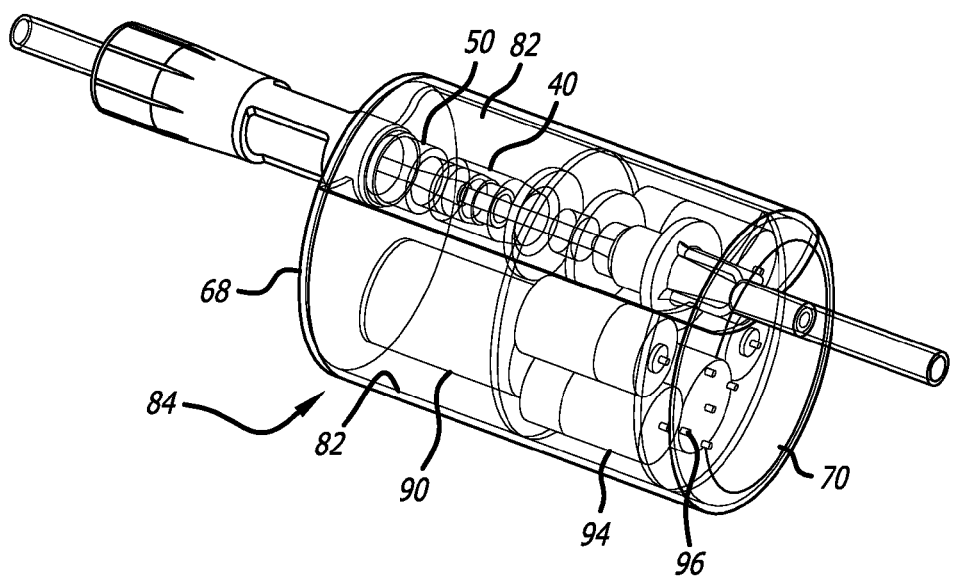
FIG. 6 is a prospective view, with the housing being transparent, depicting the transfer set connector and the Y-set connector mounted in the elliptical-shaped housing along with the UV light source and power source.
Figure 9:
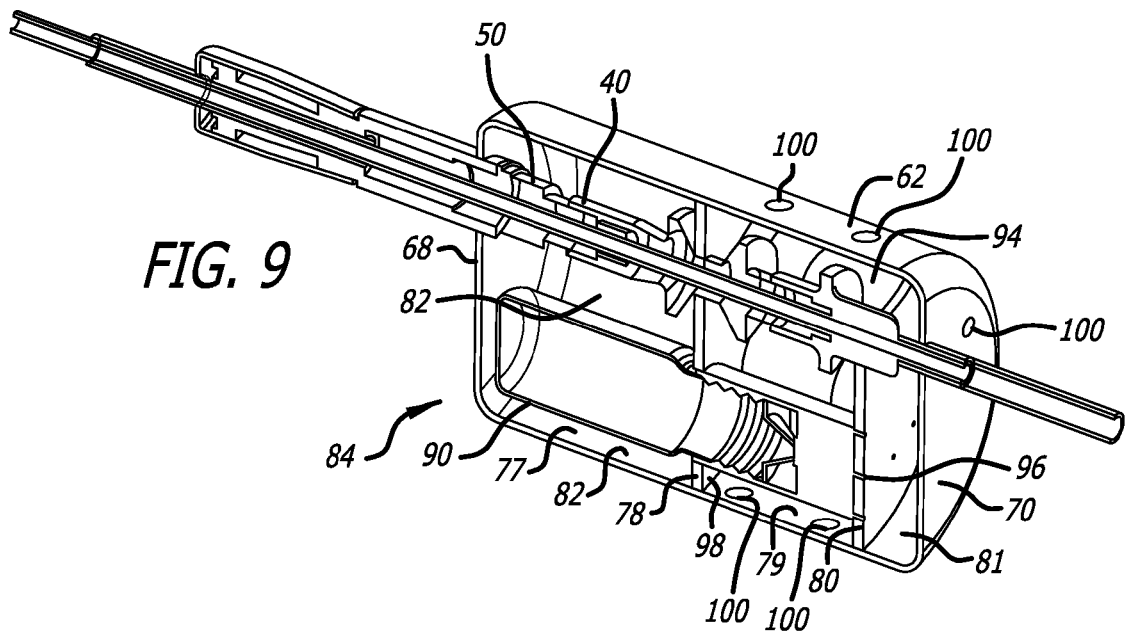
FIG. 9 is a perspective cross sectional view of the transfer set connector and the Y-set connector mounted in the elliptical housing with the UV light source positioned below the connectors.

Referring to FIGS. 2-3, a transfer set connector 50 is attached to second end 32 of tube 14 and includes a proximal end 52 for insertion into the Y-set connector 40. More specifically, the proximal end 52 of the transfer set connector is inserted into the distal end 56 of the Y-set connector 40 in order to secure the connection and provide a fluid tight seal for the transfer of fluids. An alignment mark 54 is positioned on the transfer set connector 50 and an alignment mark 58 is position on the Y-set connector 40. Both of the alignment marks are used to help position the connectors when positioning the connectors in a housing for sterilization. One feature of this embodiment is that both the transfer set connector 50 and the Y-set connector 40 are made from a UV-transmissive material. By making the connectors from a UV-transmissive material, the UV light source is better able to disinfect and sterilize the connectors as will be described more fully herein. The transfer set connector 50 and Y-set connector 40 are commonly used in PD and are made from a medical grade polymer.

Referring to FIGS. 4-10, the Y-set connector 40 and the transfer set connector 50 are connected together and placed in a housing 60. The housing 60 includes a hinged cover 62 that can be opened and closed by the patient. The housing includes an inner surface 64 and an outer surface 66. A first end 68 of the housing and a second end 70 are removably attached to the housing 60 in order to form an enclosure. The first end 68 and the second end 70 can be attached to the housing by any known method such as with fasteners or by mating parts that snap into and out of place. The Y-set connector and the transfer set connector are positioned in the housing in apertures. This can be seen for example in FIG. 4, a first aperture 72, a second aperture 74, and a third aperture 76 are formed by the arcuate portions formed in the hinged cover 62 in the housing 60. The first, second, and third apertures are configured and sized to be of different diameters and to correspond to the diameters of the transfer set connector 50 and the Y-set connector 40. For example, first aperture 72 has a greater diameter than third aperture 76, in this embodiment, in order to accommodate the greater diameter of the transfer set connector 50 as compared to the smaller diameter of the Y-set connector 40. By providing different diameters for the first, second, and third apertures, it will insure ensure that the patient properly mounts the Y-set connector 40 and the transfer set connector 50 in the housing. In a further effort to assist the patient in properly aligning the connectors in the housing, the alignment marks 54, 58 are aligned with the first end 68 and second end 70, respectively. A first partition 78 and a second partition 80 divide the housing into a first chamber 77, a second chamber 79, and a third chamber 81. In order to enhance the UV light in disinfecting and sterilizing the Y-set connector 40 and the transfer set connector 50, a reflective coating 82 is placed on at least a portion of the inner surface 64 of the housing 60. In one embodiment, the reflective coating 82 is placed on the inner surface 64 in only the first chamber 77. Further, no reflective coating is placed on the inner surface of the first end 68 or on any portion of the first partition 78. In other embodiments, it may be important to put a reflective coating 82 on the inner surface of the first end 68 and the inner surface of the first partition 78 so that all of the surfaces of the first chamber 77 have a reflective coating. However, it is preferred that the reflective coating 82 be placed only on the inner surface 64 of the housing 60 in order to maximize the reflective qualities of the UV light source. The reflective coating 82 can be formed from any number of known materials such as aluminum, etched aluminum, chrome, stainless steel, any type of mirroring metals or materials, or reflective coating or paint.

Figure 10:
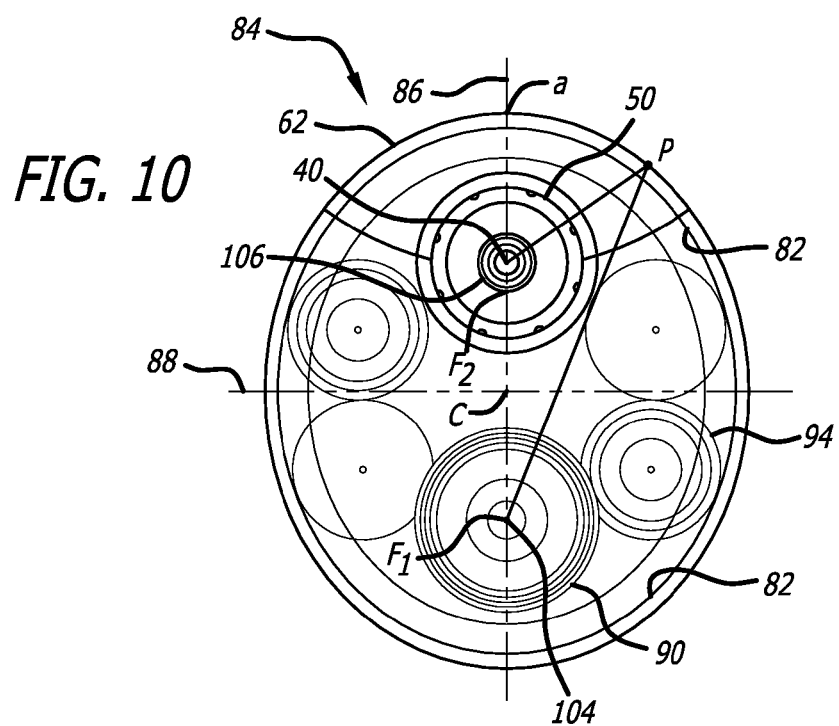
FIG. 10 is a elevational view and partial transparent view depicting the elliptical housing wherein the UV light source is positioned within the housing at a first foci, $F_1$, and the transfer set connector and Y-set connector positioned within the housing at a second foci, $F_2$.

As it can be seen more clearly in FIG. 10, the elliptical shaped housing 84 has a major axis 86 and a minor axis 88. The dimensions of the elliptical-shaped housing 84 may vary based on factors such as the length of the connectors, the diameters of the connectors, the type of UV light source and power source used, all of which must be balanced with a housing size that is comfortable and easy to use by the patient. In one embodiment, the length along the major axis ranges from 1.5 inches to 12.0 inches, and the length along the minor axis ranges from 1.0 inch to 6.5 inches. The distance between the first end 68 and the second end 70 ranges from 4.0 inches to 8.0 inches. The housing 84 and cover 62 are made from any number of medical grade polymers that are known in the art. The housing and cover are made from a rigid plastic that is light impermeable so that no UV light shines through the housing and cover during use.

With further reference to FIGS. 4-10, a UV light source 90 is mounted in housing 60, preferably in first chamber 77. It is preferred that no portion of the UV light source 90 contact any portion of the inner surface 64 of the first chamber 77. The UV light source 90 is operated by a power source 92 which can include batteries 94. An electrical circuit 96, which may include a circuit board and controller, are used to control the electrical signals from the batteries to the UV light source 90. The UV light source preferably is ultraviolet C ("UVC") and has a wavelength in the range of 100 nanometers ("nm") to 280 nm, which provides a disinfection efficiency of about 90% to 99.999%. The UV light source can include any of light emitting diodes (LED), mercury lamps, and fluorescent lamps (without an internal phoshor coating). In one embodiment, a mercury lamp has a power level in the ranges set forth in Table 1, to disinfect or sterilize the connectors 40,50.

TABLE 1

| Organisms: | Energy Dosage of Ultraviolet radiation (UV dose) in μWs/cm² needed for kill factor | |
| --- | --- | --- |
|  | 90% (1 log reduction) | 99% (2 log reduction) |
| Bacteria | | |
| *Bacillus anthracis* - Anthrax | 4,520 | 8,700 |
| *Bacillus anthracis* spores - Anthrax spores | 24,320 | 46,200 |
| *Bacillus magaterium* sp. (spores) | 2,730 | 5,200 |
| *Bacillus magaterium* sp. (veg.) | 1,300 | 2,500 |
| *Bacillus paratyphusus* | 3,200 | 6,100 |
| *Bacillus subtilis* spores | 11,600 | 22,000 |
| *Bacillus subtilis* | 5,800 | 11,000 |
| *Clostridium tetani* | 13,000 | 22,000 |
| *Corynebacterium diphtheriae* | 3,370 | 6,510 |
| *Ebertelia typhosa* | 2,140 | 4,100 |
| *Escherichia coli* | 3,000 | 6,600 |
| *Leptospiracanicola* - infectious Jaundice | 3,150 | 6,000 |
| *Microccocus candidus* | 6,050 | 12,300 |
| *Microccocus sphaeroides* | 1,000 | 15,400 |
| *Mycobacterium tuberculosis* | 6,200 | 10,000 |
| *Neisseria catarrhalis* | 4,400 | 8,500 |
| *Phytomonas tumefaciens* | 4,400 | 8,000 |
| *Proteus vulgaris* | 3,000 | 6,600 |
| *Pseudomonas aeruginosa* | 5,500 | 10,500 |
| *Pseudomonas fluorescens* | 3,500 | 6,600 |
| *Salmonella enteritidis* | 4,000 | 7,600 |
| *Salmonela paratyphi* - Enteric fever | 3,200 | 6,100 |
| *Salmonella typhosa* - Typhoid fever | 2,150 | 4,100 |
| *Salmonella typhimurium* | 8,000 | 15,200 |
| *Sarcina lutea* | 19,700 | 26,400 |
| *Serratia marcescens* | 2,420 | 6,160 |
| *Shigella dyseteriae* - Dysentery | 2,200 | 4,200 |
| *Shigella flexneri* - Dysentery | 1,700 | 3,400 |
| *Shigella paradysenteriae* | 1,680 | 3,400 |
| *Spirillum rubrum* | 4,400 | 6,160 |
| *Staphylococcus albus* | 1,840 | 5,720 |
| *Staphylococcus aureus* | 2,600 | 6,600 |
| *Staphylococcus hemolyticus* | 2,160 | 5,500 |
| *Staphylococcus lactis* | 6,150 | 8,800 |
| *Streptococcus viridans* | 2,000 | 3,800 |
| *Vibrio comma* - Cholera | 3,375 | 6,500 |
| Molds | | |
| *Aspergillius flavus* | 60,000 | 99,000 |
| *Aspergillius glaucus* | 44,000 | 88,000 |
| *Aspergillius niger* | 132,000 | 330,000 |
| *Mucor racemosus* A | 17,000 | 35,200 |
| *Mucor racemosus* B | 17,000 | 35,200 |

TABLE 1-continued

| | Energy Dosage of Ultraviolet radiation (UV dose) in $\mu Ws/cm^2$ needed for kill factor | |
|---|---|---|
| Organisms: | 90% (1 log reduction) | 99% (2 log reduction) |
| *Oospora lactis* | 5,000 | 11,000 |
| *Penicillium expansum* | 13,000 | 22,000 |
| *Penicillium roqueforti* | 13,000 | 26,400 |
| *Penicillium digitatum* | 44,000 | 88,000 |
| *Rhisopus nigricans* | 111,000 | 220,000 |
| Protozoa | | |
| *Chlorella Vulgaris* | 13,000 | 22,000 |
| Nematode Eggs | 45,000 | 92,000 |
| *Paramecium* | 11,000 | 20,000 |
| Virus | | |
| Bacteriopfage - *E. Coli* | 2,600 | 6,600 |
| Infectious Hepatitis | 5,800 | 8,000 |
| Influenza | 3,400 | 6,600 |
| Poliovirus - Poliomyelitis | 3,150 | 6,600 |
| Tobacco mosaic | 240,000 | 440,000 |
| Yeast | | |
| Brewers yeast | 3,300 | 6,600 |
| Common yeast cake | 6,000 | 13,200 |
| *Saccharomyces carevisiae* | 6,000 | 13,200 |
| *Saccharomyces ellipsoideus* | 6,000 | 13,200 |
| *Saccharomyces* spores | 8,000 | 17,600 |

Optionally, a heat sink 98 may be positioned at one or more locations within the housing 60. For example, some or all of first partition 78 may include a heat sink 98 in order to dissipate heat from the UV light source.

In one embodiment, it may be advantageous to include vent apertures 100 in the outer surface 66 of the housing 60 in order to vent any heat buildup inside the second or third chambers.

In another embodiment, an optional edge seal 102 is placed on all mating surfaces between the housing 60 and the hinge cover 62 in order to keep the environment inside the housing 60 free from contaminants, as well as seal the housing and the hinged cover so that no UV light is emitted from the housing 60 during operation.

As more clearly shown in FIG. 10, the UV light source 90 is positioned within the elliptical housing 84 at a first foci, $F_1$, and the Y-set connector 40 and transfer set connector 50 are positioned at a second foci, $F_2$. By positioning the UV light source and the connectors at the first and second foci of the elliptical-shaped housing 84, will ensure that the maximum amount of UV light is focused and reflected onto the connectors during the disinfecting and sterilizing process. In one embodiment, the distance between $F_1$ and $F_2$ is calculated according to the formula $PF_1+PF_2=Za$, where P is any point on the ellipse and "a" is the point on the ellipse where the major axis crosses the ellipse, as shown in FIG. 10. If the length along the major axis is in the range 1.5 inches to 12.0 inches and the length along the minor axis is in the range 1.0 inch to 6.5 inches, then $F_1$ and $F_2$ each are spaced from "a" in the range of 0.25 inch to 3.0 inches.

Figure 11:
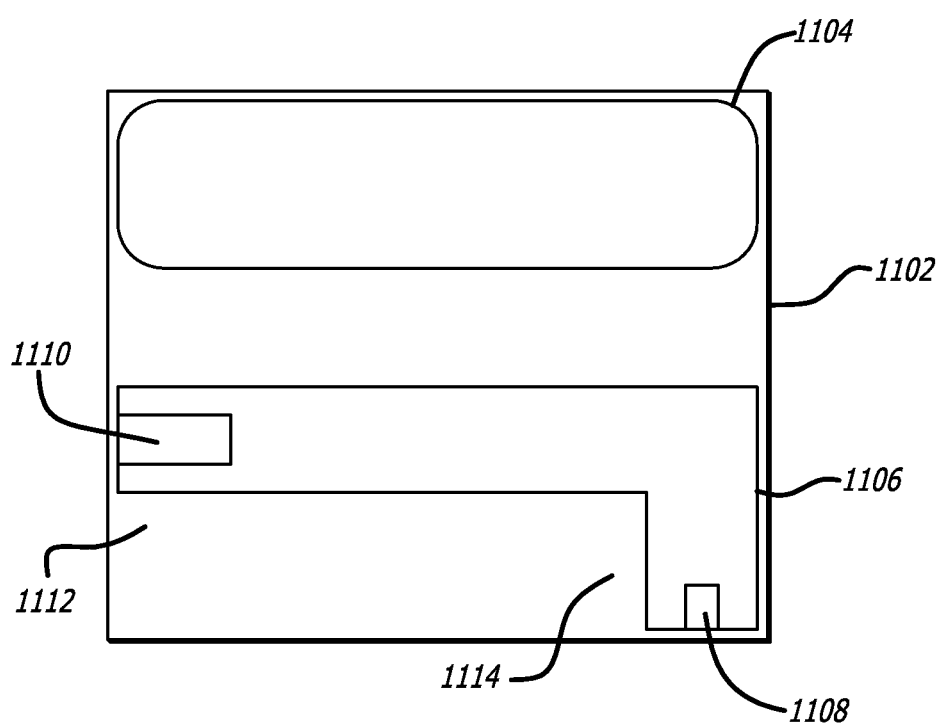
FIG. 11 is a schematic view of a housing in which UV light is applied to an L-shaped transfer set connector and Y-set connector.

FIG. 11 is a schematic view of a housing 1100 in which UV light is applied to an L-shaped transfer set connector 1112 and Y-set connector 1114. The housing 1100 can comprise a reflective box 1102 comprising a UV light source 1104, such as a UV lamp. FIG. 11 depicts a flow cell piece 1106 with inlets 1108, 1110 for the connectors.

Figure 12:
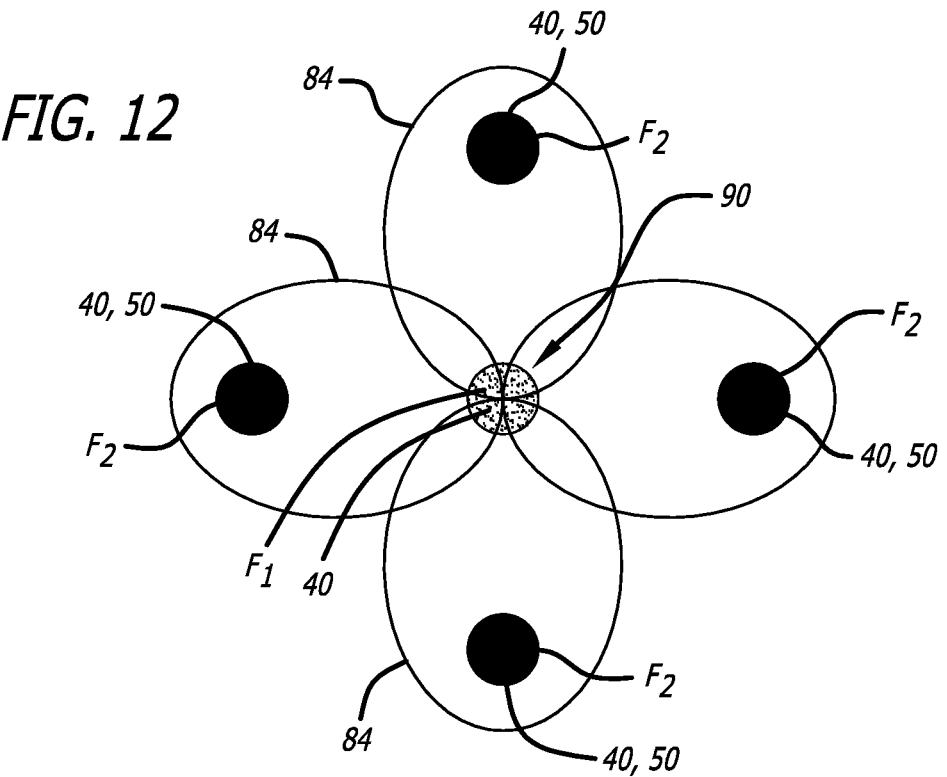
FIG. 12 is a schematic view of a housing having four chambers to disinfect or sterilize up to four sets of connectors simultaneously.

As shown in FIGS. 12-17, a CCPD (night dialysis with four bags) system includes multiple connections that are sterilized at the same time. Just like the CAPD (daytime sterilization with one connection) sterilization assembly embodiments in FIGS. 4-10, each of these four separate connections also could be made and sterilized separately. This system simply allows for all the connections to be sterilized at the same time. FIG. 12 shows four elliptical-shaped housings 84 around a central UV light source 90.

Figure 13:
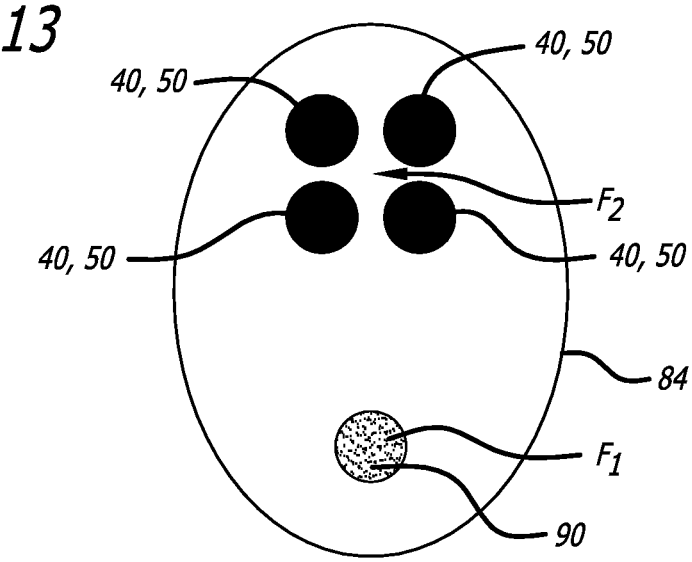
FIG. 13 is a schematic view of an elliptical shaped housing for disinfecting or sterilizing up to four connectors simultaneously.

FIG. 13 shows four connectors 40,50 positioned equidistant from second foci $F_2$ in elliptical-shaped housing 84, and UV light source 90 positioned at the first foci $F_1$.

The connectors 40,50 could also be rotated by 180° (or more) to make sure all regions of the connections receive the same sterilization dose. The rotation could be done with a stepper motor or other mechanism. Half way through the sterilization, the connectors could be rotated or turned.

In FIGS. 14 and 15, to increase the light intensity in the system, multiple UV light bulbs may also be used. Also multiple connections (such as for CCPD) could be used in the system (not shown).

One problem with the elliptical-shaped housing is that if the connector materials are not 100% transparent (i.e., transmissive to UV light), the side closest to the light source would receive more light, while the backside would receive less light. More light would be targeted to the front of the connectors (closest to the light source), and the less transmissive the materials, the less light reaches the backside of the connectors (furthest from the light source). In order to reduce the total disinfection or sterilization time, and better distribute the light more evenly, the following systems could be used. For example, as shown in FIGS. 16 and 17, multiple light sources could surround the connector plane. These light sources could also be smaller in diameter than those used in the elliptical housing embodiments. The reflector housing could also be shaped to provide a parabolic shape around each light bulb to reflect light towards the center of the connector plane.

The multi-bulb system of FIGS. 16 and 17 would be useful if the light source were pulsed white light (which can be quite small). This would alleviate the need to have UVC transmissive connectors, and the sterilization mechanism of pulsed white light is slightly different than UV, which could also lead to a very efficacious system provided enough light is delivered.

Alternatively in FIGS. 16 and 17, pulsing a UV light source to deliver high intensity UV light in short bursts is also envisioned.

Instead of using multiple light sources as shown in prior embodiments, two (or more) fluorescent light sources as shown in FIGS. 18-27 (one on the top half of the housing, and the other on the bottom half) could be used that snake back and forth and surround the connectors. This would reduce the power requirements of the system while maximizing the light output toward the connectors. With any of these systems, the light source would likely be shielded behind some type of barrier to protect the light source, and if its broken protect the patient and connectors from the light supply.

Figure 18:
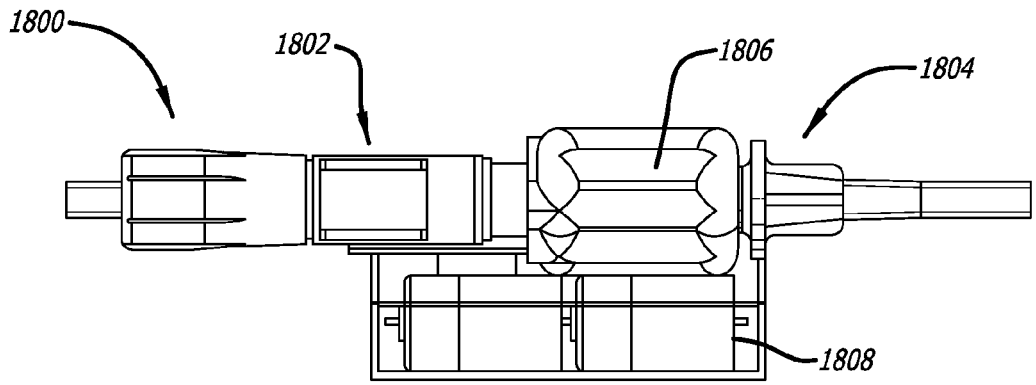
FIG. 18 is a side elevational view of a transfer-set connector and a Y-set connector mounted in a housing with outer reflectors for reflecting the light source.
Figure 19:
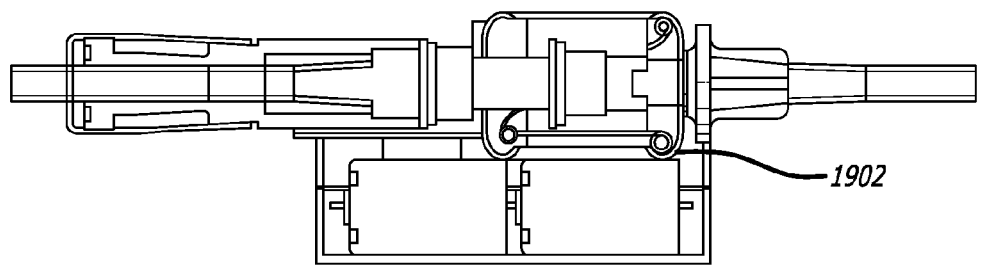
FIG. 19 is a cross-sectional view of the assembly of FIG. 18, depicting the light source and reflectors surrounding the transfer-set and Y-set connectors.

FIG. 18 is a side elevational view of a transfer-set connector 1802 and a Y-set connector 1804 mounted in a housing 1800 with outer reflectors 1806 for reflecting the light source. FIG. 18 also depicts batteries 1808. FIG. 19 is a cross-sectional view of the assembly of FIG. 18, depicting the light source 1902 and reflectors 1806 surrounding the transfer-set and Y-set connectors.

Figure 20:
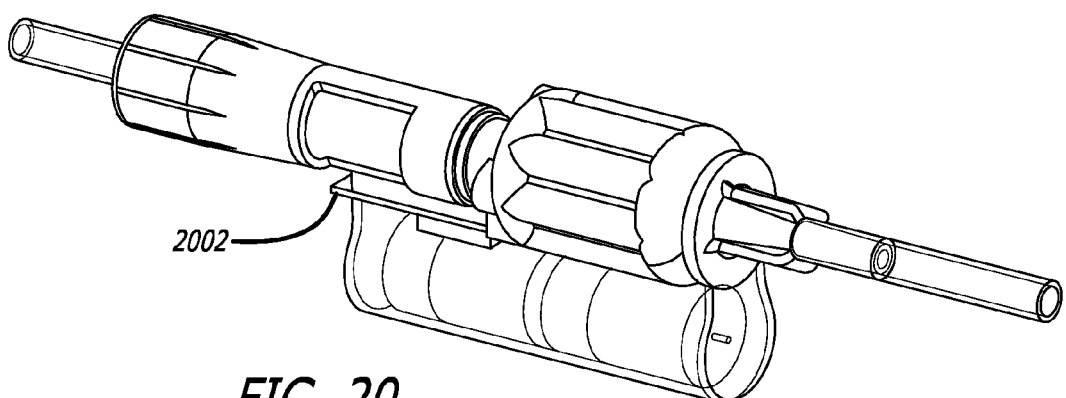
FIG. 20 is a perspective view and partial transparent view of transfer-set and Y-set connectors surrounded by a light source for disinfecting or sterilizing the connectors.

FIG. 20 is a perspective view and partial transparent view of transfer-set and Y-set connectors surrounded by a light source for disinfecting or sterilizing the connectors. FIG. 20 shows a circuit board 2002.

Figure 21:
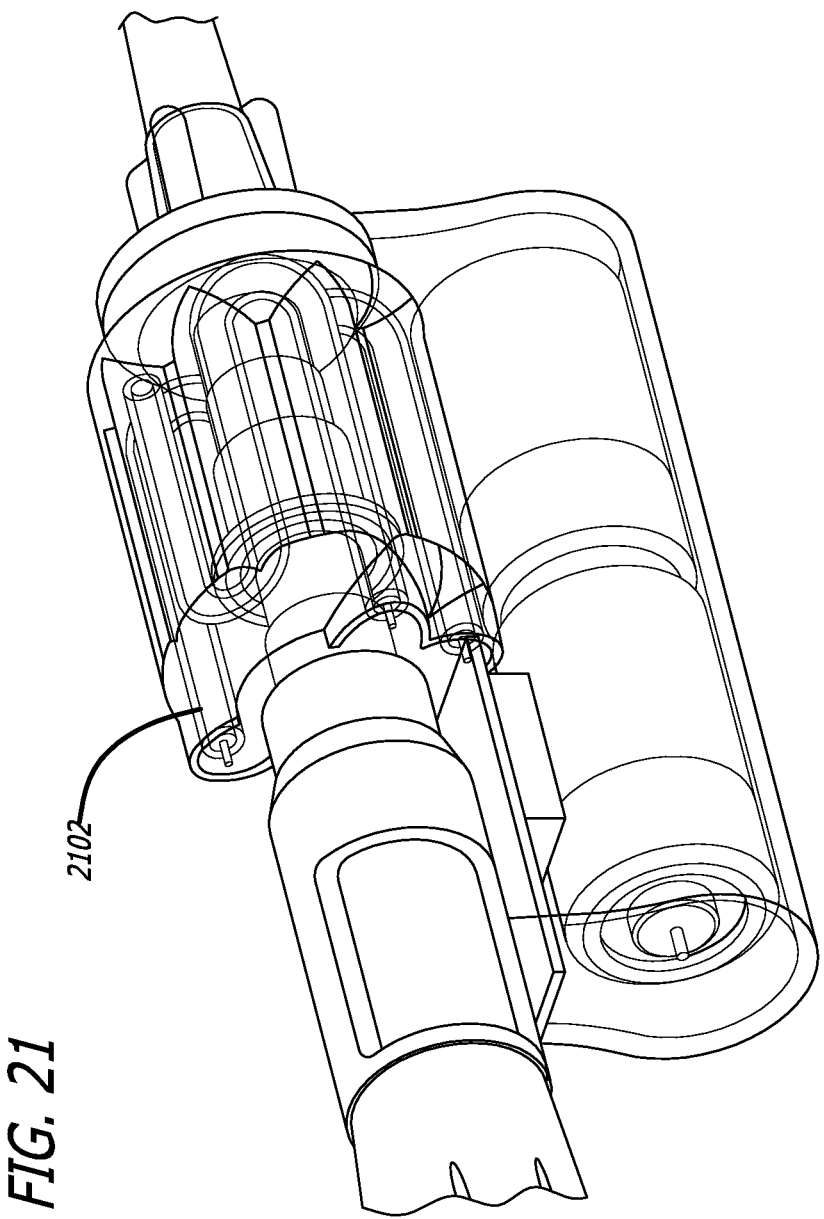
FIG. 21 is a perspective and partial transparent view depicting a transfer-set connector and Y-set connector surrounded by the light source and reflectors.
Figure 22:
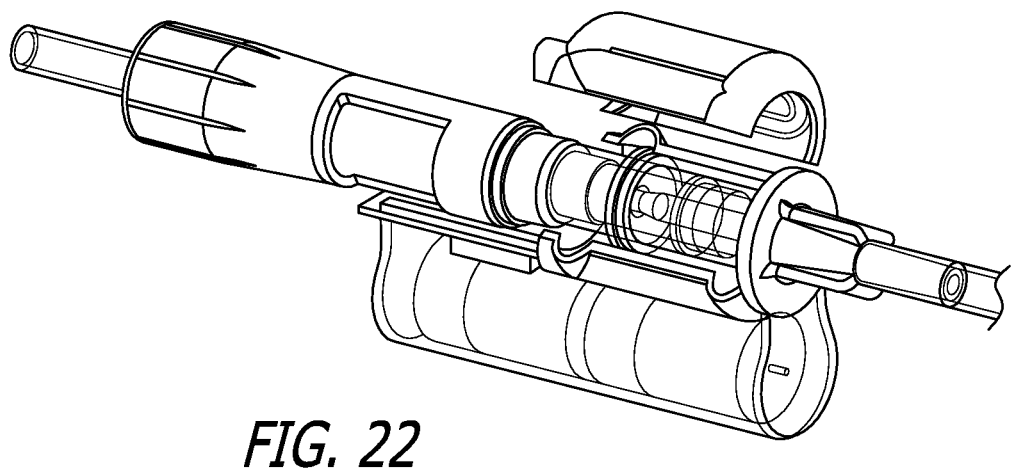
FIG. 22 is a perspective view and partial transparent view depicting the Y-set connector and transfer-set connector surrounded by the reflectors and light source.
Figure 23:
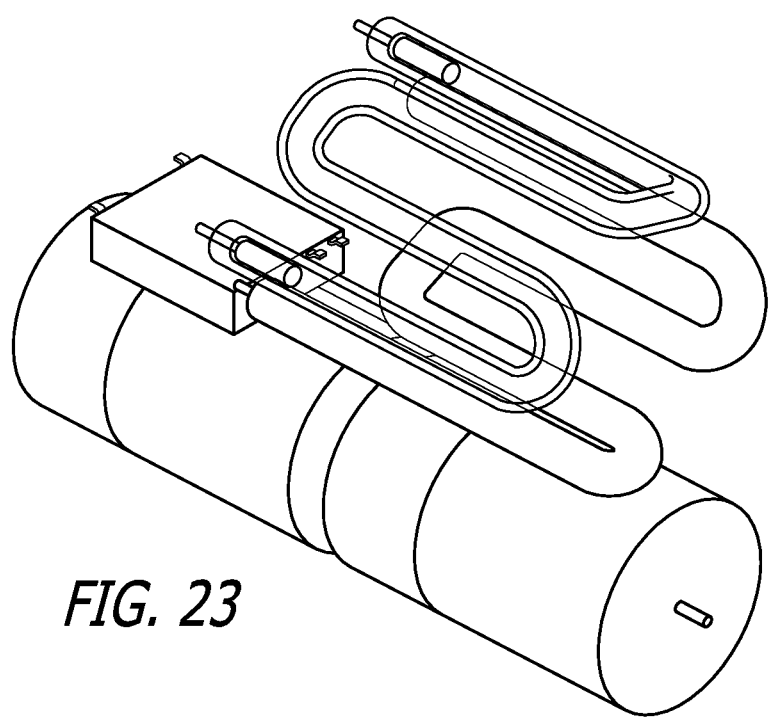
FIG. 23 is a partial perspective view depicting a serpentine light bulb configured for surrounding a transfer-set connector and Y-set connector.

FIG. 21 is a perspective and partial transparent view depicting a transfer-set connector and Y-set connector surrounded by the light source and reflectors. FIG. 21 illustrates serpentine shaped light bulbs 2102 snaking around the connection. In the perspective and partially transparent view of FIG. 22 hinged reflectors and light bulbs in a clamshell configuration that can be opened to insert and remove the connection are shown. FIG. 23 is a partial perspective view depicting a serpentine light bulb configured for surrounding a transfer-set connector and Y-set connector. FIG. 23 illustrates the serpentine light bulb shape without the connectors or reflectors.

Figure 24:
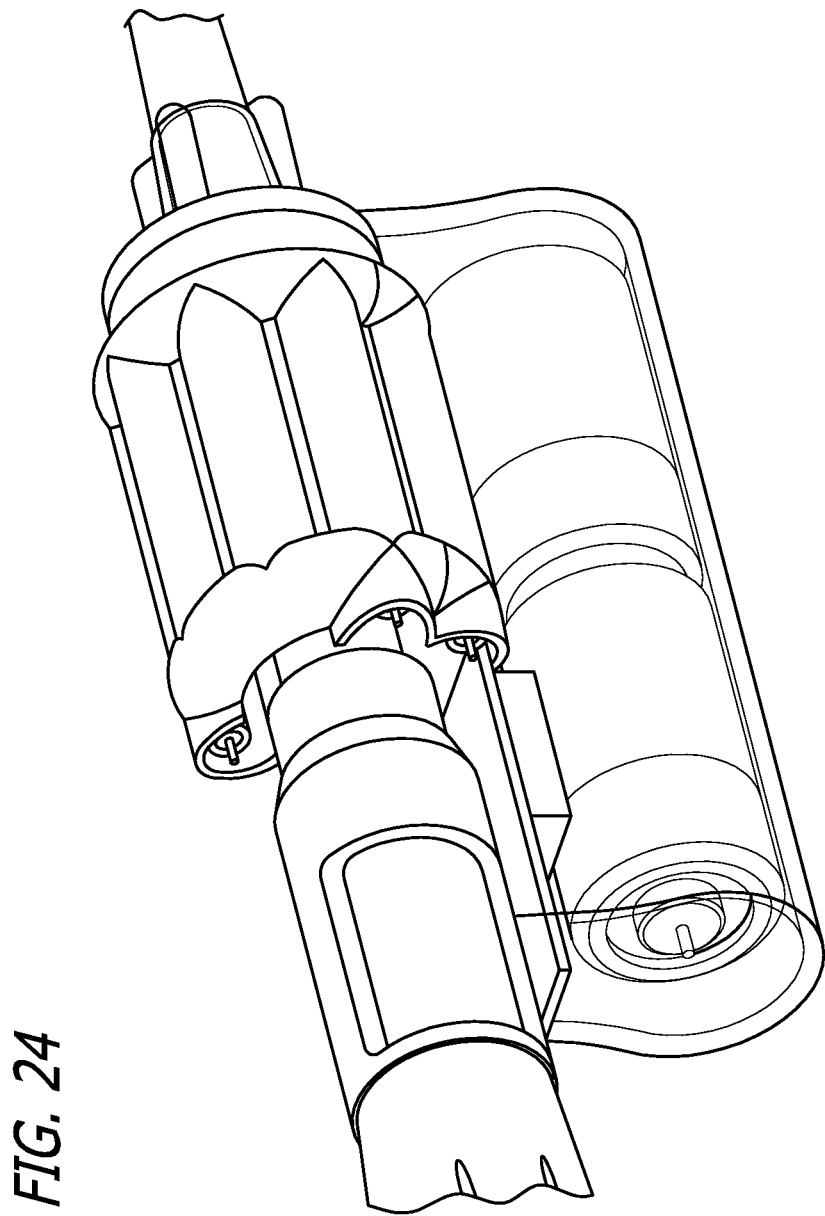
FIG. 24 is a perspective view, and partial transparent view, depicting a transfer-set connector and Y-set connector surrounded by a light source.

FIG. 24 is a perspective view, and partial transparent view, depicting a transfer-set connector and Y-set connector surrounded by a light source. FIG. 24 is a perspective view, and partial transparent view, depicting a transfer-set connector and Y-set connector surrounded by a light source.

Figure 25:
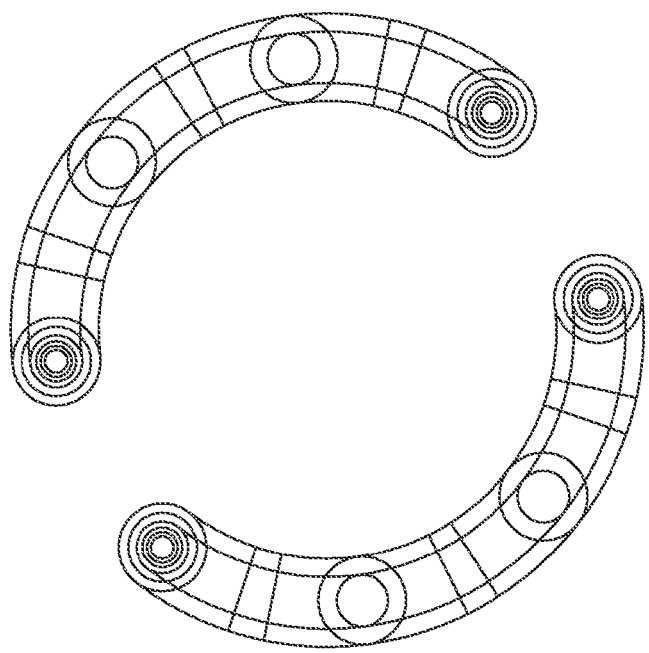
FIG. 25 is a partial cross-sectional view depicting a light bulb arrangement.

FIG. 25 is a partial cross-sectional view depicting the light bulb arrangement.

Figure 26:
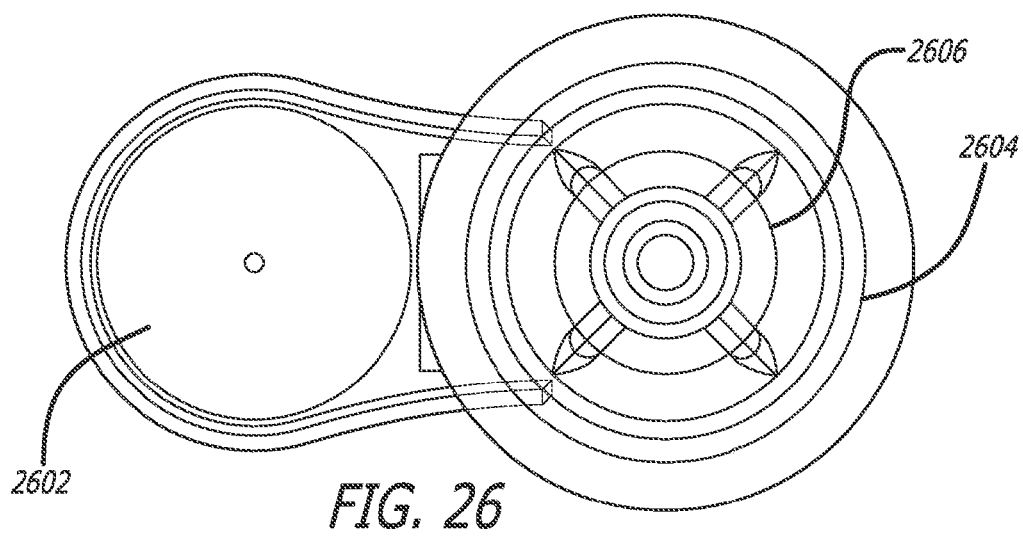
FIGS. 26-27 are cross-sectional views and partial transparent views depicting the connectors surrounded by a light source and reflective housing.
Figure 27:
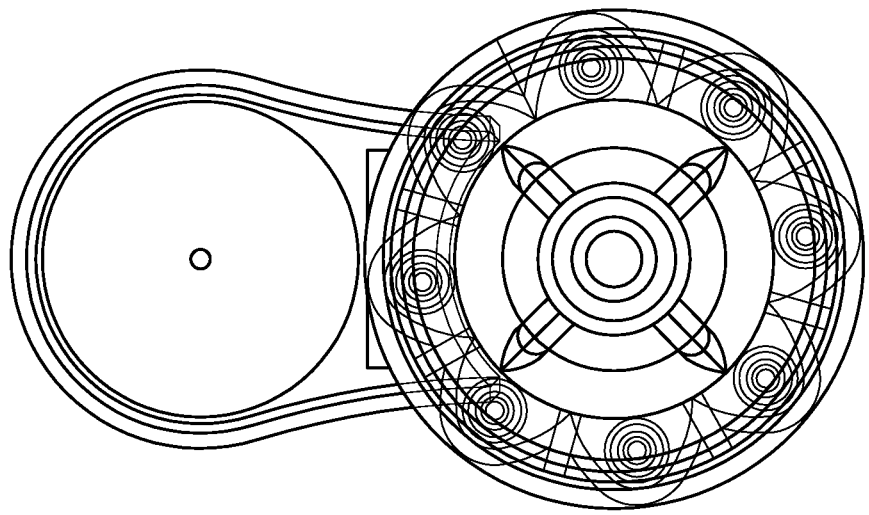

FIGS. 26-27 are cross-sectional views and partial transparent views depicting the connectors surrounded by a light source and reflective housing. FIG. 26 illustrates batteries 2602, reflective housing 2604, connector plane 2606 and light source 2608.

In one embodiment, shown in FIGS. 28-37, the light could be helical-shaped, which surrounds the connectors, and the connectors would both slide inside the helical bore before being screwed together. There could be a quartz sleeve between the light and the central bore to protect the light source and provide a nice clean bore, and reflectors on the outer side of the light source. This system could also be miniaturized to live on the patient's transfer set 2802. The Y-set connector 2804 would be inserted into the lumen and during dialysis, the sterilization would happen automatically. A cap could be used to block the entrance to this bore, and the cap would also be UV transmissive and would trigger sterilization automatically. There could also be a removable battery back that the patient could charge when not in use.

Figure 28:
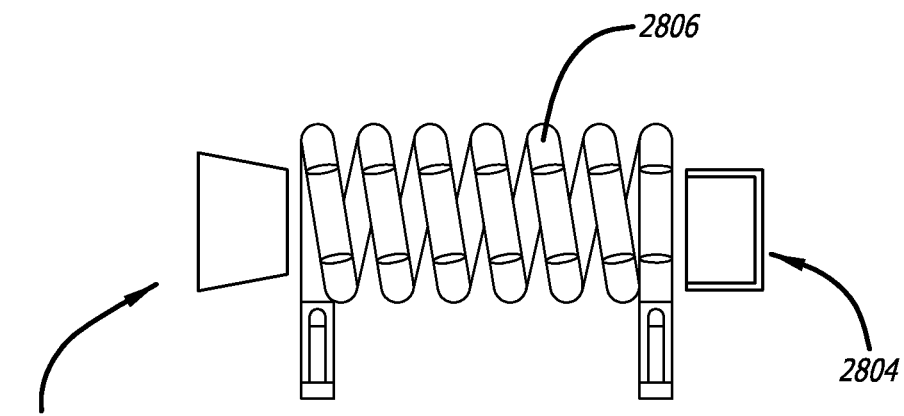
FIG. 28 is a partial elevational view depicting a transfer-set connector and Y-set connector surrounded by a helical light source.

FIG. 28 is a partial elevational view depicting a transfer-set connector and Y-set connector surrounded by a helical light source 2806.

Figure 29:
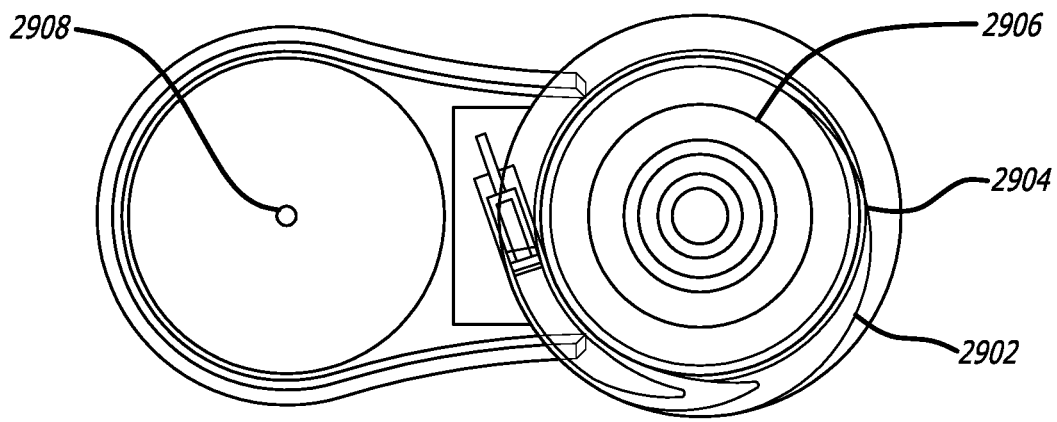
FIG. 29 is a cross-sectional view of a connector surrounded by a light source and reflective housing.

FIG. 29 is a cross-sectional view of a connector surrounded by a light source 2904 and reflective housing 2902. FIG. 29 depicts the connector plane 2906 and the batteries 2908.

Figure 30:
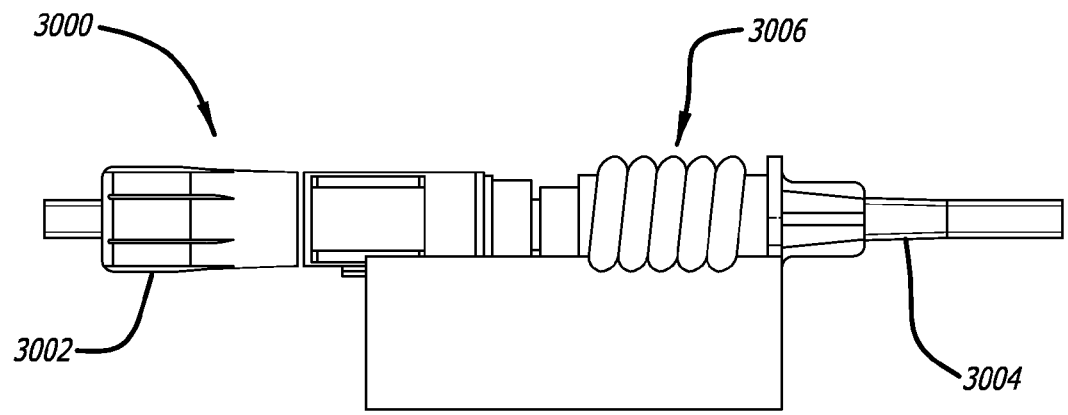
FIGS. 30-37 are different views of a transfer-set connector and a Y-set connector inside a helical sterilization system including a parabolic-shaped reflector.
Figure 31:
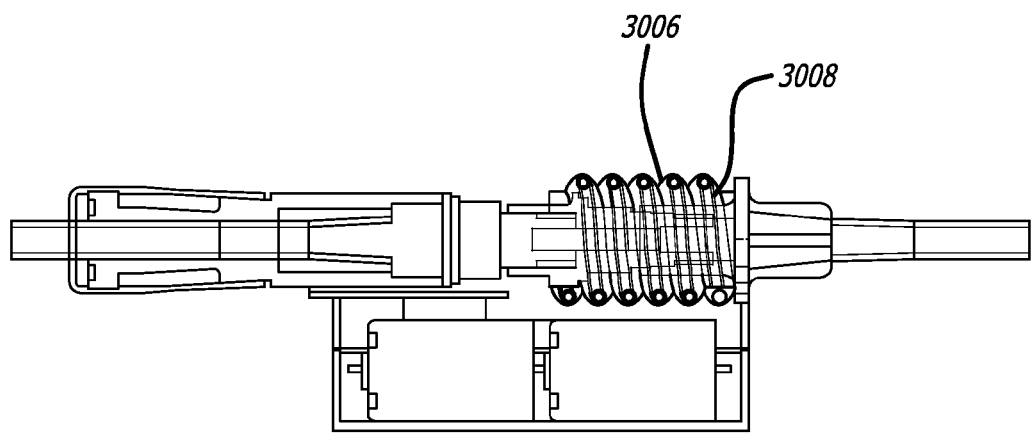
Figure 32:
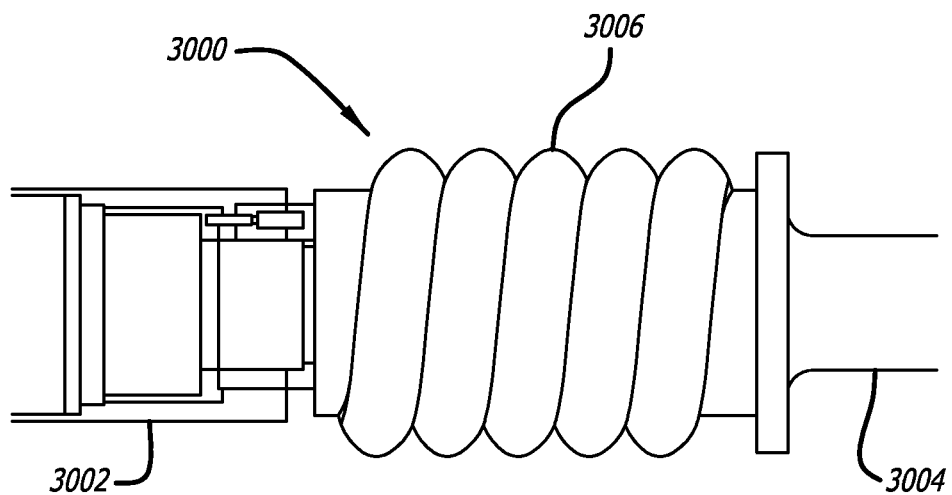
Figure 33:
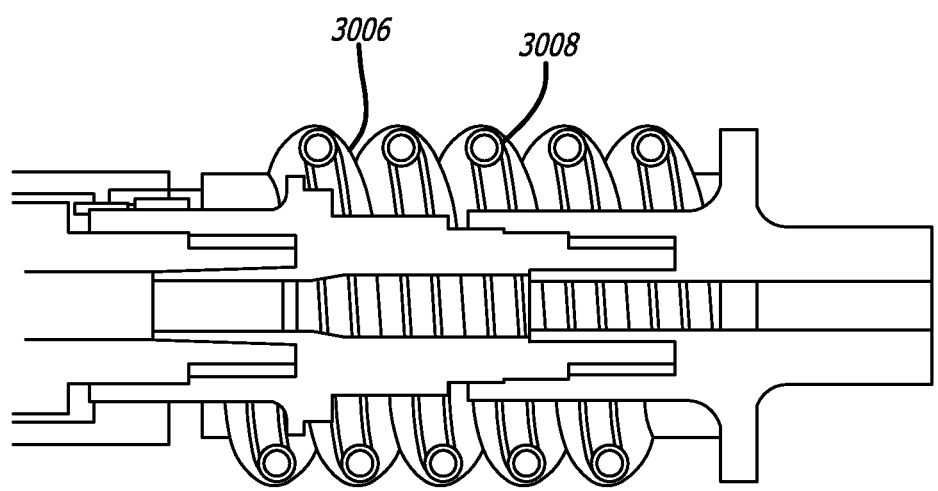
Figure 34:
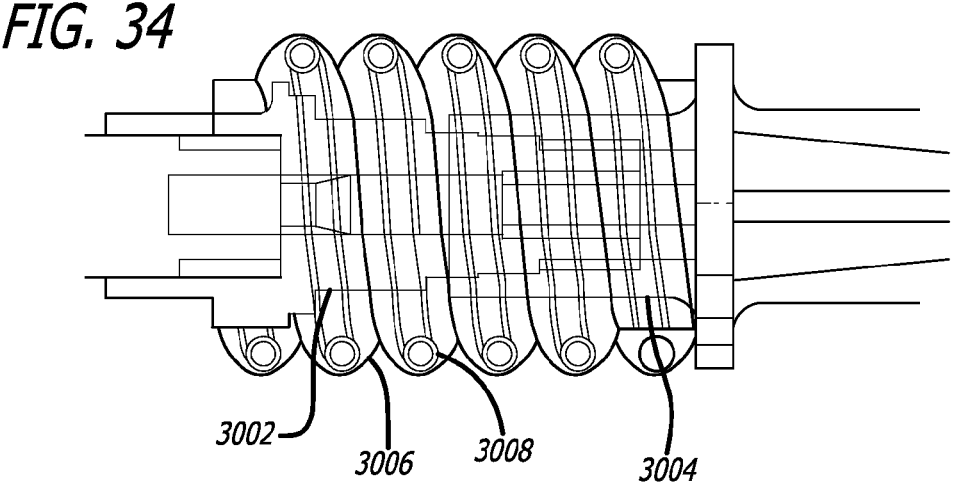
Figure 35:
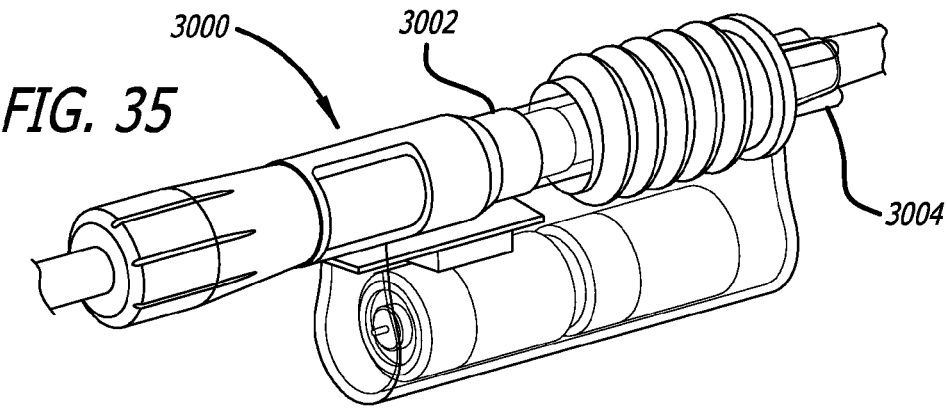
Figure 36:
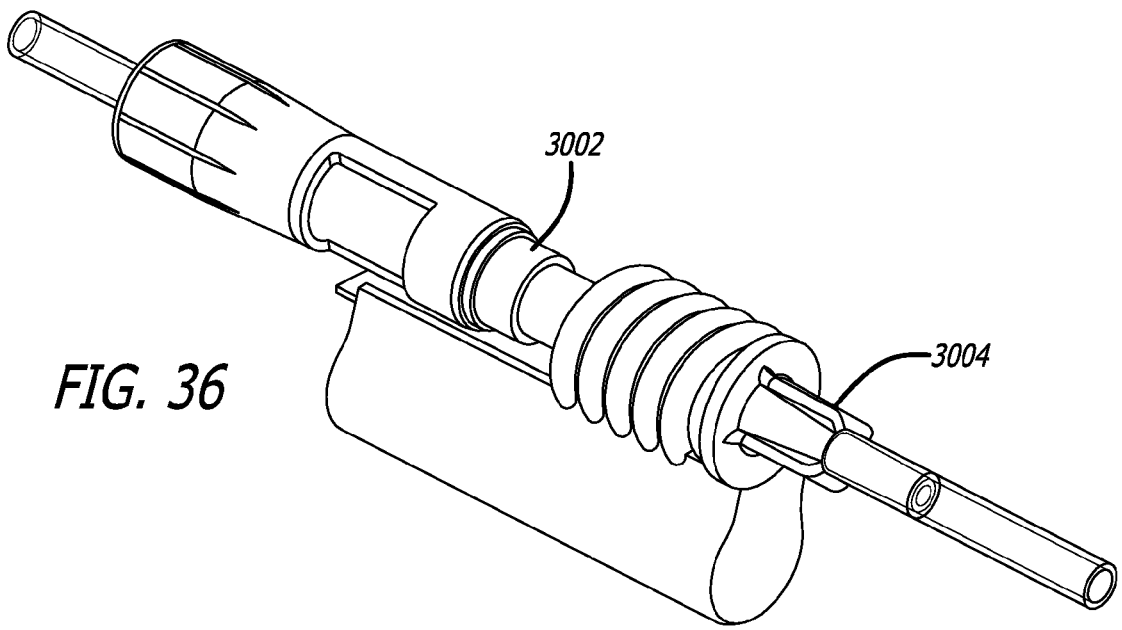
Figure 37:
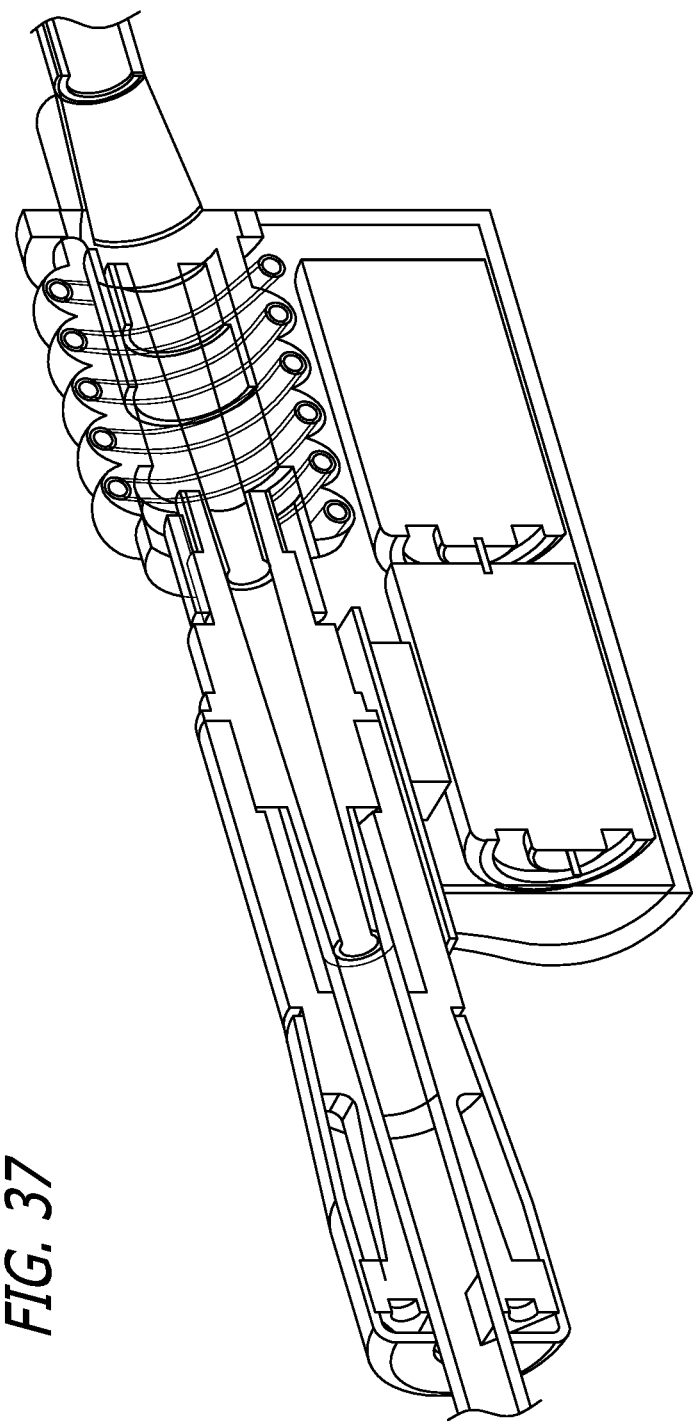

FIGS. 30-37 are different views of a transfer-set connector 3002 and a Y-set connector 3004 inside a helical sterilization system 3000 including a parabolic-shaped reflector. FIG. 30 illustrates the light source and reflector 3006. FIG. 31 shows a transparent side view of the reflector 3006, showing the light source 3008 and the connectors inside the reflectors 3006. FIG. 32 illustrates a side view of the system 3000 with the transfer set connector 3002 and the Y-Set Connector 3004 connected instead the system 3000. FIG. 33 illustrates the helical light source 3008 and the parabolic shaped reflector 3006 around the light source 3008, the parabolic shaped reflector 3006 to direct all light toward the connector plane. FIG. 34 is an enlarged view of the connectors 3002, 3004 positioned in the system 3000. FIGS. 35 and 36 are isometric views of the connectors 3002, 3004 in the sleeve-like sterilization system 3000. There could be features on the transfer set 3002 that secure the sterilization sleeve in place before the Y-set 3004 is inserted and connected to the transfer set 3002. FIG. 37 is a cutaway perspective view of the system 3000.

Figure 38:
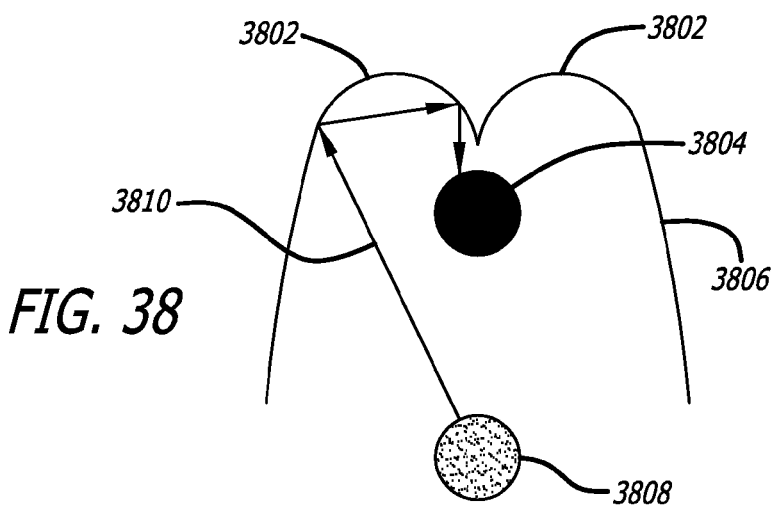
FIG. 38 is a schematic view of connectors in a housing in which the light source is reflected off of parabolic reflectors.

FIG. 38 is a schematic view of connectors in a housing in which the light source is reflected off of parabolic reflectors. In one embodiment, shown in FIG. 38, one or more parabolic reflectors 3802 are used to increase the light distribution on the back side (side farthest from the light source). The housing 3806 could be shaped like a double parabola. A double reflection of the light from the light source 3808 would guide light that hits the side walls toward the backside of the connector 3804, as shown in the reflection pattern 3810.

For assemblies having non-luer connectors, the connection could be made with another mechanism that is not a luer lock. One end can be made of a harder plastic, or quartz, while the other end is made of a UV transmissive elastomer like FEP. The elastomer then forms a secure bond by stretching over the harder connector.

In many of the embodiments disclosed herein, a cap is placed over the transfer set to ensure patient compliance with the disinfection or sterilization process. At the end of the dialysis, the patient would place a UVC transmissive cap over the transfer set. The user would then sterilize the transfer set and cap again. This alleviates the need for Beta-Dyne caps, and could be a more effective sterilization method.

To ensure patient compliance, features on the cap, and/or cap insertion tool, make the patient use the system to remove the cap. This system could be similar to medicine bottles that have features where you need to squeeze or push down the cap in order to be able to remove it. Features in the sterilization system could be used to accomplish this. Removing the tubing clamps from the transfer-set and the Y-set and placing them on the sterilization device would also ensure patient compliance to the system.

To improve transmissive properties of the connectors, instead of using a homogeneous material, the material could be filled with very transparent particles such as quartz. This could lead to a very transmissive and strong material that is easier to work with than quartz or glass.

If the sterilizing device were to live on or off the patient, making the battery or power supply easily removable and easily chargeable (such as using inductive charging) is preferred.

In one embodiment, multiple small white light LED's to be used in a pulsed white light system are placed on a flexible circuit. This flexible circuit with LED's could be wrapped over quartz tubing, like tape, to create a disinfection lumen so the connectors could be placed within. This would create a very small system that could live on the patients at all times. Further UV-LED's could be placed on the flexible circuit as well.

Figure 39:
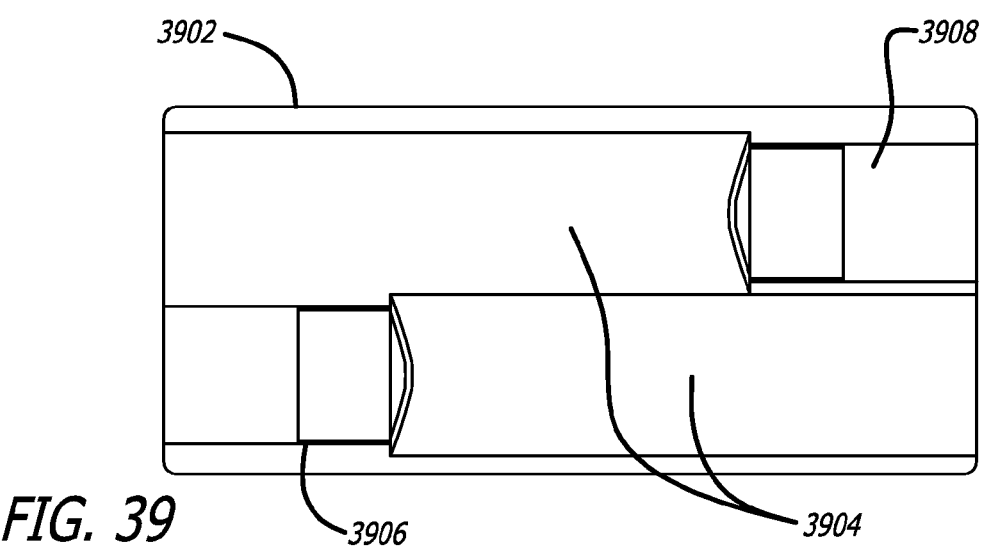
FIGS. 39 and 40 are elevational views, partially in section, depicting a dual parallel dialysate chamber for disinfecting or sterilizing a transfer-set during peritoneal dialysis.
Figure 40:
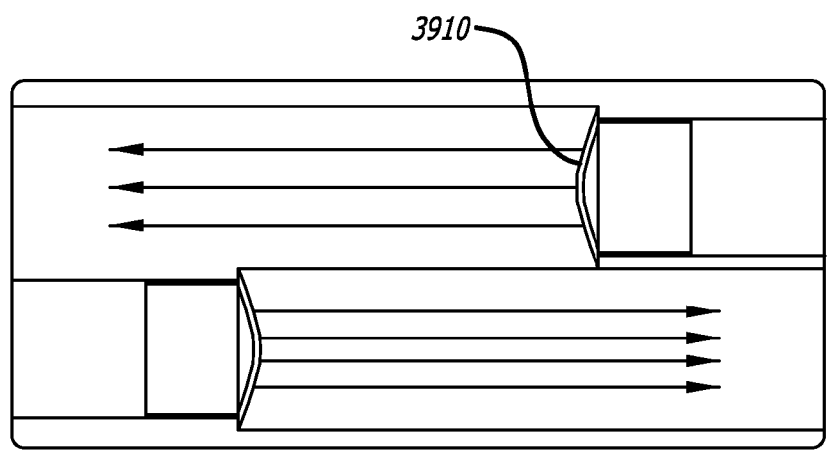

FIGS. 39 and 40 are elevational views, partially in section, depicting a dual parallel dialysate chamber 3902 for disinfecting or sterilizing a transfer-set during peritoneal dialysis. The embodiment shown in FIGS. 39 and 40 utilizes a dual parallel configuration for UV application along a dialysate chamber to disinfect surfaces of a transfer set during peritoneal dialysis. The dialysate chamber 3902 is fabricated of fused silica, or comparable material high transmissive in the UVC range. The flow path of the dialysate is directed through a linear path wherein the path is offset between the catheter end and the transfer end. (FIG. 39) This allows UV-LEDs to be positioned optimally at one end of each of the parallel paths 3904 to direct UV rays along the longitudinal direction of each path. Fluid flow is generally unperturbed by the linear geometry of the path, and it also limits stagnant flow or pooling of residual dialysate fluid by which bacteria may have a source for nutrients. To accommodate this, the internal surfaces of the dialysate chamber through which the dialysate flows is of a cylindrical geometry. The two parallel offset paths overlap slightly such they maintain continuity and therefore allow the flow from the catheter end to the transfer end. At the closed end of each parallel path is an pocket or counterbore 3908 for placement of an UV-LED 3906. These counterbores can be optimally configured to create a lens effect where it joins with the dialysate path. For instance, the wall 3910 of fused silica or other material between the parallel path and the LED Pocket 3908 can be of a hemispherical shape. This would allow direction of the UV rays in a tighter focal area and maintain higher energy applied within the borders of the parallel path 3904 and towards the connectors at the open end of the path. (FIG. 40).

FIGS. 41 and 42 are elevational views, partially in section, depicting fiber optic cables wrapped in coils in a dialysate chamber. The embodiment shown in FIGS. 41 and 42 utilizes UV transmission via fiber optic cables 4106 to disinfect a chamber 4108 through which dialysate would flow during peritoneal dialysis. The dialysate chamber is comprised of a fused silica material with a lumen, spanning a linear length, and is set within a housing 4102. This assembly serves as a transfer set between the indwelling dialysis catheter and a dialysate bag junction. Fiber optic cables 4106 capable of transmitting light in the UV-C range of the spectrum may be formed of silica, known to result in minimum attenuation of UV in this range. Fiber cores are available in a variety of sizes, from 50-1500 um. An external source of UV provides the energy, which is transmitted along a bundle of fibers. The fibers can be separated and wrapped around the dialysate chamber to distribute the UV along the length of the chamber. A reflective layer 4104 may be employed to maintain the UV transmission towards the surfaces of the chamber. (FIG. 41) Additionally, any of the individual fibers may have a reflective coating 4202 to effectively distribute UV application along the chamber rather than to concentrate along the first end of the dialysate chamber where the fibers are initially separated. (FIG. 42)

The reflective coating may comprise a laminated layer or a deposited layer of highly reflective composition, such as silicon oxide. Alternatives to the helical wrap configuration depicted, the fibers may also be configured as longitudinal elements parallel to the longitudinal axis of the dialysate chamber. In such a configuration, the lengths of the individual fibers may be varied to distribute the UV along the length of the chamber. The benefit of these configurations is to separate the source of the UV from the dialysate chamber. This allows the user to connect the bundled end of the cables from the transfer set housing to an external box and eliminating the need for circuitry within the transfer set itself.

Figure 43:
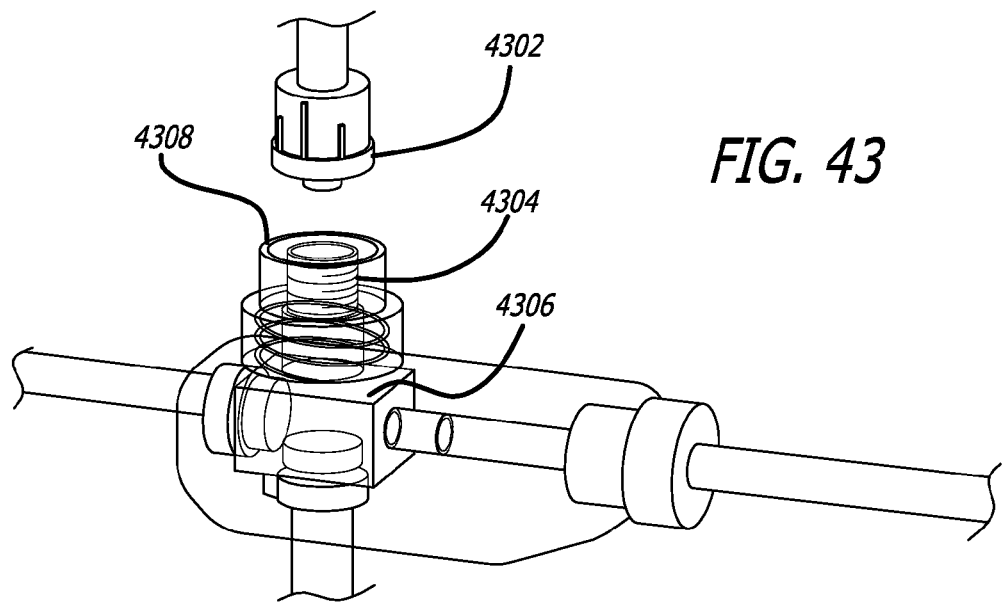
FIG. 43 is an exploded perspective view, partially transparent, depicting a transfer-set and Y-set connector.
Figure 44:
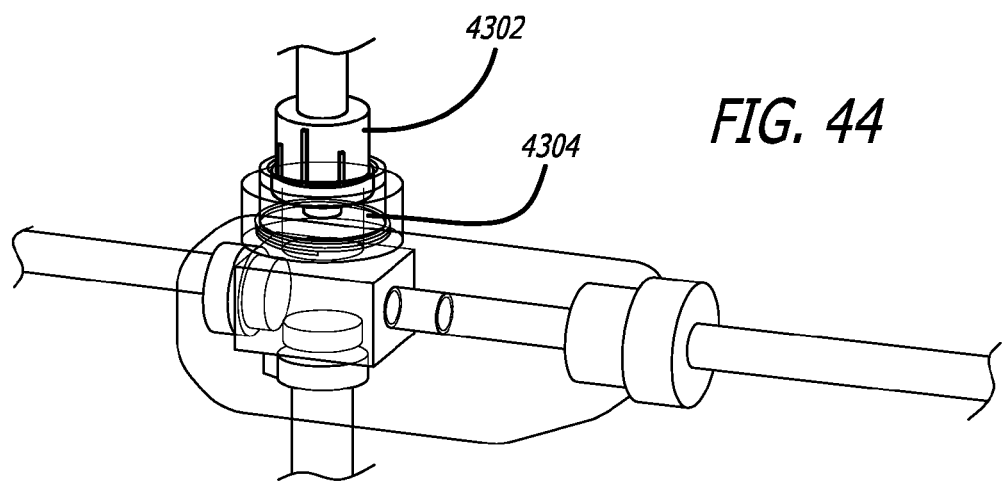
FIG. 44 is a perspective view, partially transparent, depicting a transfer-set and Y-set connector.
Figure 45:
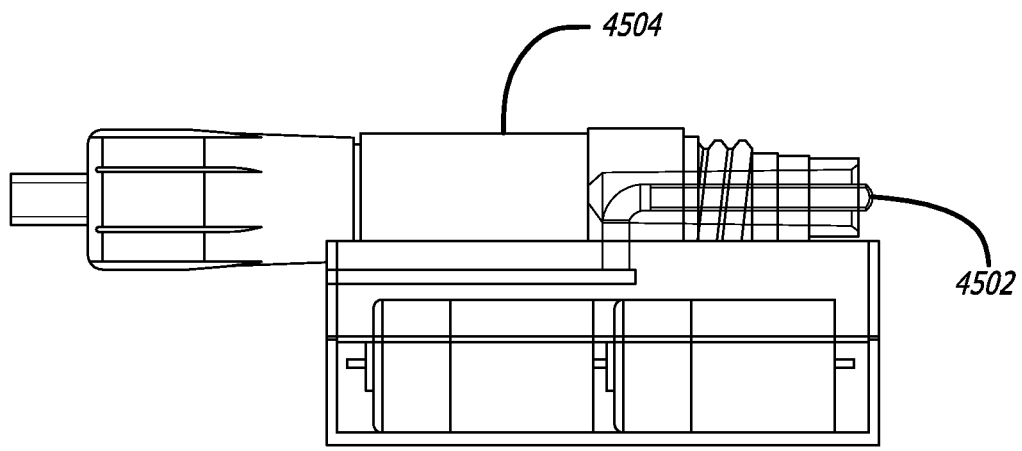
FIGS. 45-50 depict a light source positioned coaxially within a lumen of a connector.
Figure 46:
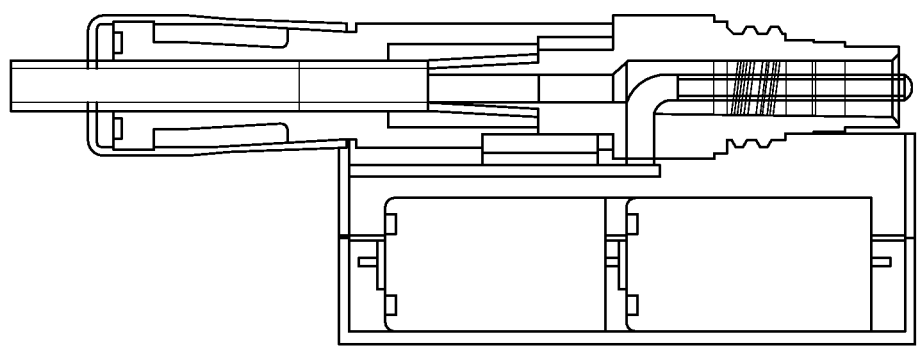
Figure 47:
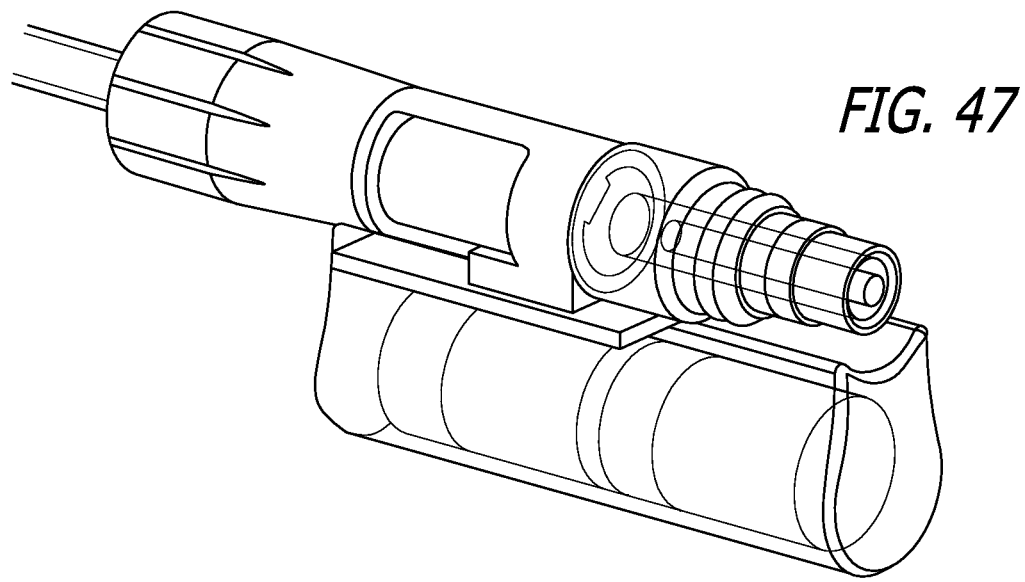
Figure 48:
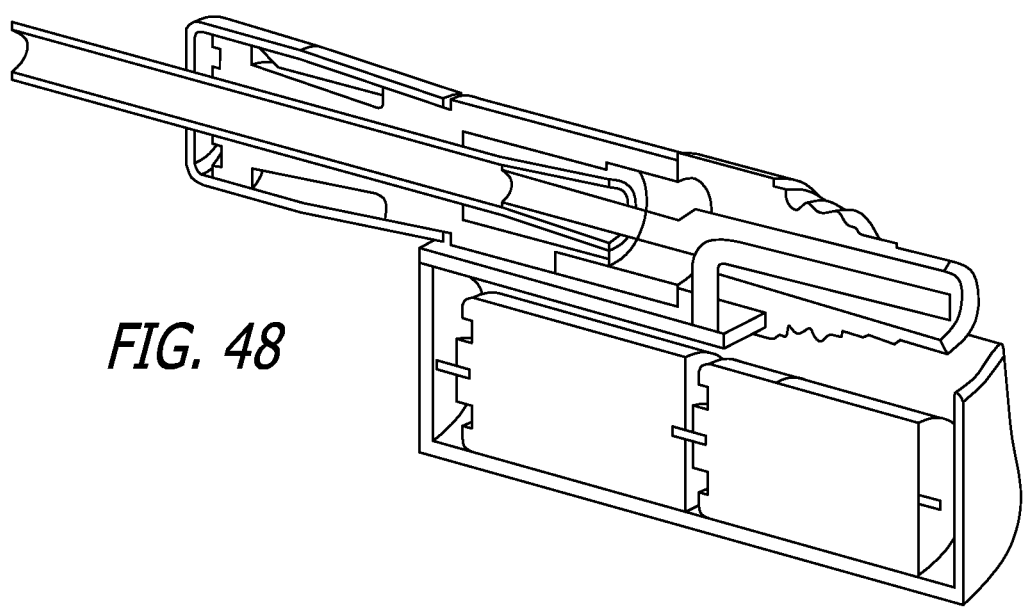
Figure 49:
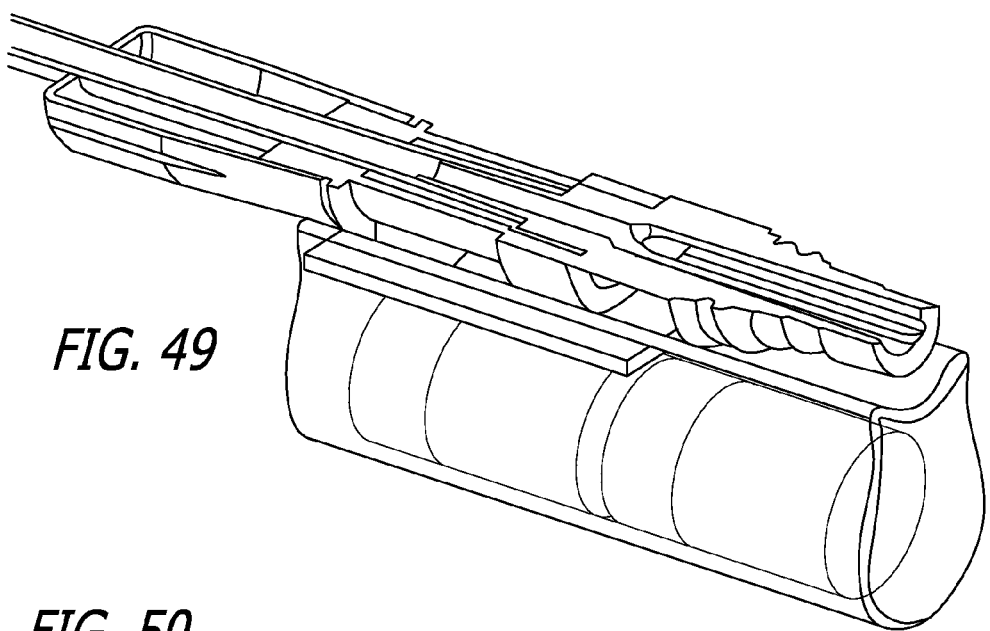
Figure 50:
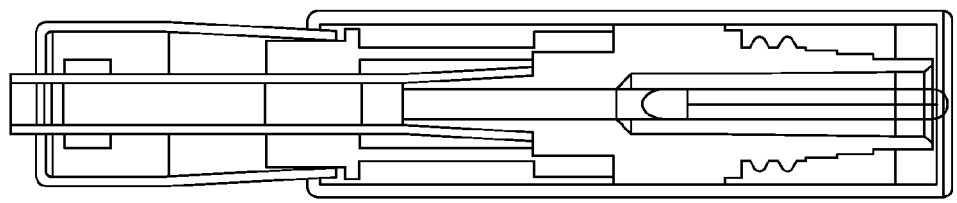

The embodiment shown in FIGS. 43 and 44 focuses on the prevent touch contamination of the transfer set female luer 4306. FIG. 43 is an exploded perspective view, partially transparent, depicting a transfer-set and Y-set connector. FIG. 44 is a perspective view, partially transparent, depicting a transfer-set and Y-set connector. As is this commonly vulnerable due to non-compliance or mishandling during preparations for peritoneal dialysis, contamination could be prevented by providing a guard or protective covering for the luer connector that could easily and automatically be moved out of the way. A spring-loaded guard 4304 comprising a cylindrical piece coupled with a compression spring is fitted into the housing of the transfer set. In its natural position, the guard 4304 is at full extension such that it completely covers the female luer from the environment (FIG. 43). Additionally, a valve 4308 covers the opening of the guard such that the luer is no exposed, yet can easily be exposed through the valve when appropriate. During non-use, the guard serves as a protective layer such that the user does not inadvertently touch the luer surfaces and so that particulates do not accumulate on the luer surfaces. When preparing for dialysis, the user is able to move the guard when attempting to make the connection between the male luer on the Y-set and the female luer on the transfer set.

There is an interference between the male luer and the guard so that as the male luer is aligned and pushed towards the transfer set luer, the guard is also pushed into the recess in the housing, compressing the spring. Meanwhile, the female luer is gradually exposed through the valve of the guard as it is pushed deeper in the housing. Upon completion of dialysis, the guard automatically returns to the forward and protective position when the male luer is disconnected, due to the spring force unloading. (FIG. 44)

In one embodiment, shown in FIGS. 45-50, a light source 4502 is positioned in the middle of the connector lumen in order to disinfect or sterilize the connector from the inside out. A UV light source is positioned coaxially inside the connector lumen, such as the transfer set 4504 connector lumen so that UV light radiates radially outwardly toward the connector inner lumen surface.

Figure 51:
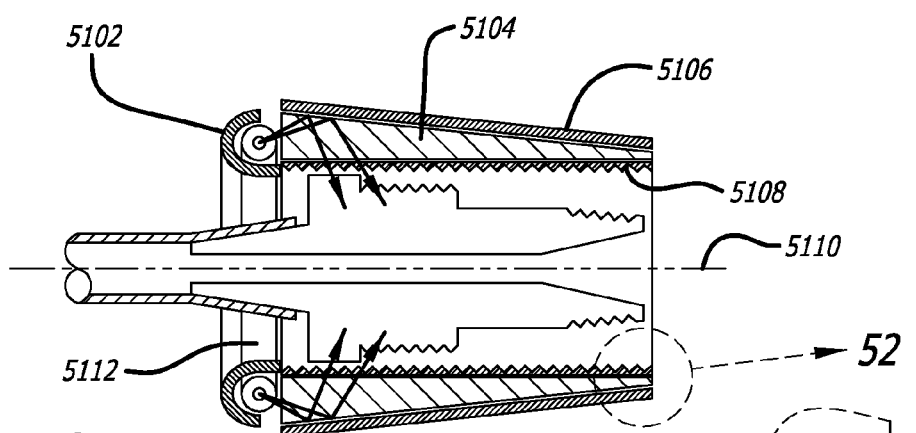
FIGS. 51-52 depict a cross-sectional view of an annular light guide.
Figure 52:
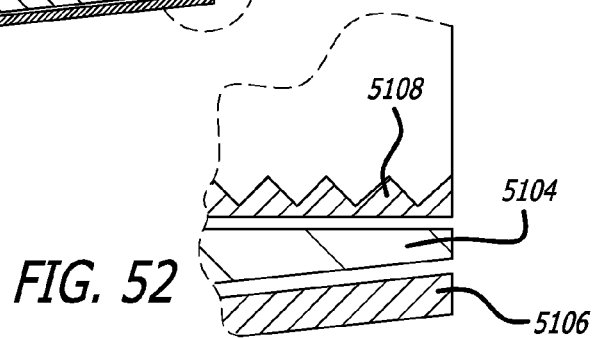

FIG. 51 depicts a cross-sectional view of an annular light guide system 5100. The light guide 5100 comprises a circular, elliptical, or parabolic reflector 5102. The system 5100 comprises a UV transmissive (e.g., quartz) light guide 5104 that is edge lit. The system 5100 comprises a reflector 5106 positioned next to the light guide 5104. The system 5100 can comprise an optional prismatic film 5108 positioned on the inside of the light guide 5104. FIG. 52 shows a blow-up view of the reflector 5106, light guide 5104, and optional prismatic film 5018. The system 5100 comprises a cold cathode Hg Vapor discharge tube 5112. Alternatively the system 5100 can comprise PWL or a Hg Vapor flash lamp, which can be pulsed. The system 5100 can be used for faster disinfection, by providing higher power or from the circular configuration. A blown up view of the light recycling or prismatic film 5108, the light guide 5104, and the reflector 5106.

Several experiments have been conducted to determine the UVC transmissivity of various polymers and multiple layers of quartz tubes using off the shelf UV light sources.

Experiment 1

Transmission Test with Spectrophotometer

Abstract

The purpose of this experiment was to determine the UVC transmissivity of various UV transmissive polymers. Topas 8007X10, PMP RT18, and PMP DX820 plaques of 2 mm thickness were obtained and cut into small pieces approximately 12.5 mm by 45 mm (the height and width of a standard cuvette). The pieces were placed into a Jenway Genova spectrophotometer against the left wall of the cuvette slot. The spectrophotometer was set to read at 255 nm, with an empty slot as the reference. The results show that 2 mm samples of Topas 8007X10, PMP RT18, and PMP DX820 have transmissivity rates of 49%, 27%, and 30%, respectively. The Brand UV cuvette macro, which was placed into the spectrophotometer intact, had a transmission rate of 42%.

Protocol

1. Material Preparation
   1.1. Using a Dremel rotary tool with a cutting tip, cut 12.5 mm by 45 mm pieces from each of the 2 mm thick plaques (Topas 8007X10, PMP RT18, and PMP DX820).
   1.2. Make sure that the pieces fit into the cuvette slot of the Jenway Genova spectrophotometer.
   1.3. Remove anything which is currently inside the cuvette slot. Set the spectrophotometer to read at 255 nm, and press REF.
   1.4. Place the Topas 8007X10 piece into the cuvette slot, against the left wall of the slot.
   1.5. Record the transmission %.
   1.6. Repeat steps 1.4-1.5 for PMP RT18, PMP DX820, and an intact Brand UV cuvette macro. (For the cuvette, just place the entire cuvette inside the slot).
   1.7. Repeat steps 1.4-1.6 two additional times for a total of three readings per material sample.

Results

|  | Transmittance % | | | |
|---|---|---|---|---|
|  | Trial 1 | Trial 2 | Trial 3 | Average |
| Topas 8007X10 | 49 | 47 | 51 | 49 |
| PMP RT18 | 28 | 27 | 27 | 27 |
| PMP DX820 | 29 | 30 | 31 | 30 |
| Brand UV Cuvette | 42 | 42 | 42 | 42 |

Conclusion

The results from this experiment verify that Topas 8007X10 has the highest transmission rate at 255 nm out of the material samples. The transmission numbers from this experiment are slightly different from those obtained in transmission tests using the LED and the Thor Labs S120VC sensor. It is important to note that the pieces cut in this experiment were not the exact width of the cuvette slot. Therefore, the piece could not stand perpendicular to the bottom surface and had to lean against the left wall of the slot. This will affect transmission readings. However, the relative rates of transmission agree with Thor Labs sensor readings. The Topas 8007X10 is the most transmissive, followed by the Brand cuvette, PMP DX820, and PMP RT18.

Experiment 2

UV Mercury Lamp Experiment with Topas 8007X10 and PMP RT18

Abstract

The purpose of this experiment was to determine the antimicrobial effectiveness of an off-the-shelf UV lamp through two different UV transmissive polymers. Topas COC 8007X10 and TPX PMP RT18 plaques (2 mm thickness) were obtained and cut into small rectangular pieces of similar shape and size. S. Aureus liquid culture (1 uL) sitting between two layers of the same material was exposed to a Spectronics DeGERM-inator UV 5D lamp for 60 seconds or 120 seconds. After 60 seconds, the PMP sample produced a significantly higher log reduction than Topas. After 120 seconds, almost all bacterial colonies were eliminated in both samples.

Protocol

1. Biosafety:
   Spray the Biological Safety Cabinet (BSC) with 70% ethanol and wipe with kimwipe before and after the experiment. Also spray everything that goes in and out of the hood with 70% ethanol.
2. Pre-Experiment Methods:
   At least 24 hours before starting an experiment, two inoculum samples with the same organism but with different volumes will be prepared (24 hours for bacteria, 48 hours for fungi). One will have a total volume of 5 mL, and this will be used throughout the experiment the next day. The other will have a total volume of 1 mL, which will be used to increase the OD of the sample if needed.
   2.1. Obtain a stock plate of the organism and the appropriate media from the 6° C. refrigerator.
   2.2. Pour about 6 mL of media into a sterile 14 mL polypropylene tube with dual-position cap.
   2.3. Using a P1000, pipette 1 mL of media from the polypropylene tube into a sterile microcentrifuge.
   2.4. Using a sterile 1 uL disposable loop, swab several colonies from the stock plate and swirl the loop into the microcentrifuge. Place the loop into the waste beaker with 10% bleach.
   2.5. Vortex the microcentrifuge for 30 seconds.
   2.6. Label with the organism name and date.
   2.7. Using a new sterile 1 uL disposable loop, swab several colonies from the same stock plate and swirl the loop into the polypropylene tube with media. Place the loop into the waste beaker with 10% bleach.
   2.8. Completely seal the tube by pushing down on the plastic cap until you hear a pop.
   2.9. Vortex the tube for 30 seconds.
   2.10. Label the tube with the organism name and date.
   2.11. For bacteria, loosen the plastic cap and together with the microcentrifuge tube, place on the shaker inside the 37 C incubator. For yeast (C. albicans), loosen the plastic cap and allow to incubate at 25 C for 48 hours. For molds (A. niger), completely seal the tube by pushing down on the plastic cap and allow to incubate at 25 C for 48 hours.
3. Material Preparation
   Using a dremel with a cutting tip, cut six small rectangular pieces from each of the PMP RT18 and Topas 8007X10 plaques.
   3.1 Place all the pieces into a beaker filled with 70% ethanol. Let sit for at least 1 minute.
   3.2 Dry the materials with kimwipes.
   3.3 Before using, make sure that that all surfaces are dry.
4. Control and Experimental Conditions
   4.1. For each control condition, inoculate 1 uL of liquid culture onto the center of a piece of sample material. Align and place another piece of material on top, sandwiching liquid culture between the two pieces. Let sit for 5 minutes.
   4.2. For each experimental condition, inoculate 1 uL of liquid culture onto the center of a piece of sample material. Align and place another piece of material on top, sandwiching the liquid culture between the two pieces. Let sit for 5 minutes. Center UV lamp directly over the setup and approximately 2.4 inches away from the inoculation point. Expose for 60 seconds or 120 seconds.
   4.3. Collect from all samples.

5. Collection
   5.1. Using forceps which have been disinfected with 70% alcohol, transfer the two pieces sandwiching the liquid culture into a pre-labeled 50 mL Falcon tube pre-filled with 9 mL of dialysate.
   5.2. Vortex Falcon tube for 2 minute.
   5.3. Transfer 1 mL of solution from the Falcon tube into the 10^0 well.
   5.4. Using the forceps, remove the sample material from the Falcon tube and drop into a 70% ethanol bath.
6. Plating
   6.1. Label and pre-fill an autoclaved 96-well plate with 900 uL 0.85% saline.
   6.2. Vortex collected solution for 30 seconds then pipette 100 uL inoculum into the 10^-1 dilution well.
   6.3. With a new pipette tip, homogenize the solution by mixing thoroughly. Do this by pipetting the liquid up and down the well.
   6.4. Pipette 100 uL from the 10^-1 to the following well. Do this until desired dilution is reached. Do not forget to switch pipette tips before homogenizing the solution in each well.
   6.5. Pipette 100 uL from the dilutions into agar plates, then spread using a plastic spreader. Perform this three times on three separate agar plates, for each dilution. Label each plate appropriately (e.g. C1, 10^-1, A). For the 10^0 samples, make sure to vortex the falcon tube before pipetting onto the agar plates.
   6.6. Incubate the plated cultures (37 C for bacteria, room temperature for yeast and fungi) and monitor the growth on the plated cultures. The incubation time for bacteria is usually 16 hours, while for yeast and mold the incubation time is ~48 hours.
   6.7. Record time placed in incubator:
   6.8. Record time taken out of the incubator:
7. Clean-Up
   7.1. Place the material pieces into an ethanol bath.
   7.2. Soak plastic spreaders with 10% bleach, then ethanol and dry with kim wipes.
   7.3. Spray equipment with 70% ethanol.
   7.4. Make new plates, media, bleach, ethanol if necessary.
8. Bacterial Colony Formation Data Collecting
   8.1. Refer to the ATCC Product information sheet for specifics on the description of each colony. In general, colonies are entire, circular, and raised.
   8.2. Recognize the difference between two or more colonies that have grown into contact with each other.
   8.3. Have a second person check your count.
9. Data Analysis
   9.1. To calculate the bacterial cell count, divide the colony count by the dilution factor and the plated volume. The resulting units should be CFU/mL.
   9.2. Calculate the average bacterial cell count across the three plates of the same sample for each dilution factor.
   9.3. Calculate the average bacterial cell count of the same sample across dilution factors.
   9.4. Calculate the average total bacterial cell count across the control samples. This is the estimated total bacterial cell count of the original culture.

Results

| Summary Table | PMP - RT18 Control | PMP - RT18 60 s | PMP - RT18 120 s | Topas 8007X10 Control | Topas 8007X10 - 60 s | Topas 8007X10 - 120 s |
|---|---|---|---|---|---|---|
| With Outliers | | | | | | |
| Mean CFU/mL | 71052 | 229 | 9 | 43356 | 2259 | 114 |
| Kill Rate | | 99.68% | 99.99% | | 94.79% | 99.74% |
| Log Reduction | | 2.49 | 3.90 | | 1.28 | 2.58 |
| Without Outliers | | | | | | |
| Mean CFU/mL | 71052 | 6 | 9 | 43356 | 3359 | 0 |
| Kill Rate | | 99.99% | 99.99% | | 92.25% | 100.00% |
| Log Reduction | | 4.09 | 3.90 | | 1.11 | |

| Sample | Dilution | A | B | C | Mean | CFU/mL (across plates) | CFU/mL (across dilutions) | CFU/mL (across samples) |
|---|---|---|---|---|---|---|---|---|
| IC | 1.00E−01 | 233 | 227 | 242 | 234 | 23400 | 27367 | 27367 |
| IC | 1.00E−02 | 27 | 43 | 24 | 31 | 31333 | | |
| RC1 | 1.00E−01 | 547 | 356 | 528 | 477 | 47700 | 74233 | 71052 |
| RC1 | 1.00E−02 | 69 | 52 | 74 | 65 | 65000 | | |
| RC1 | 1.00E−03 | 6 | 26 | 1 | 11 | 110000 | | |
| RC2 | 1.00E−01 | 677 | 638 | 560 | 625 | 62500 | 68833 | |
| RC2 | 1.00E−02 | 50 | 66 | 61 | 59 | 59000 | | |
| RC2 | 1.00E−03 | SMEAR | 1 | 16 | 9 | 85000 | | |
| RC3 | 1.00E−01 | 767 | 582 | 689 | 679 | 67933 | 70089 | |
| RC3 | 1.00E−02 | 93 | 79 | 85 | 86 | 85667 | | |
| RC3 | 1.00E−03 | 10 | 2 | 5 | 6 | 56667 | | |
| R60-1 | 1.00E+00 | 78 | 48 | 99 | 75 | 750 | 675 | 229 |
| R60-1 | 1.00E−01 | 6 | 8 | 4 | 6 | 600 | | |
| R60-2 | 1.00E+00 | 0 | 0 | 0 | 0 | 0 | 0 | |
| R60-2 | 1.00E−01 | 0 | 0 | 0 | 0 | 0 | | |
| R60-3 | 1.00E+00 | 1 | 6 | 0 | 2 | 23 | 12 | |
| R60-3 | 1.00E−01 | 0 | 0 | 0 | 0 | 0 | | |
| R120-1 | 1.00E+00 | 8 | 4 | 4 | 5 | 53 | 27 | 9 |
| R120-1 | 1.00E−01 | 0 | 0 | 0 | 0 | 0 | | |
| R120-2 | 1.00E+00 | 0 | 0 | 0 | 0 | 0 | 0 | |
| R120-2 | 1.00E−01 | 0 | 0 | 0 | 0 | 0 | | |
| R120-3 | 1.00E+00 | 0 | 0 | 0 | 0 | 0 | 0 | |
| R120-3 | 1.00E−01 | 0 | 0 | 0 | 0 | 0 | | |
| TC1 | 1.00E−01 | 511 | 436 | 423 | 457 | 45667 | 50556 | 43356 |
| TC1 | 1.00E−02 | 56 | 58 | 54 | 56 | 56000 | | |
| TC1 | 1.00E−03 | 4 | 5 | 6 | 5 | 50000 | | |

-continued

| | | | | | | | | |
|---|---|---|---|---|---|---|---|---|
| TC2 | 1.00E−01 | 379 | 381 | 446 | 402 | 40200 | 42178 | |
| TC2 | 1.00E−02 | 40 | 45 | 34 | 40 | 39667 | | |
| TC2 | 1.00E−03 | 3 | 4 | 7 | 5 | 46667 | | |
| TC3 | 1.00E−01 | 389 | 356 | 355 | 367 | 36667 | 37333 | |
| TC3 | 1.00E−02 | 32 | 35 | 39 | 35 | 35333 | | |
| TC3 | 1.00E−03 | 6 | 4 | 2 | 4 | 40000 | | |
| T60-1 | 1.00E+00 | 9 | 13 | 3 | 8 | 83 | 58 | 2259 |
| T60-1 | 1.00E−01 | 0 | 1 | 0 | 0 | 33 | | |
| T60-2 | 1.00E+00 | 364 | 377 | 385 | 375 | 3753 | 4027 | |
| T60-2 | 1.00E−01 | 48 | 43 | 38 | 43 | 4300 | | |
| T60-3 | 1.00E+00 | 273 | 256 | 236 | 255 | 2550 | 2692 | |
| T60-3 | 1.00E−01 | 26 | 38 | 21 | 28 | 2833 | | |
| T120-1 | 1.00E+00 | 0 | 0 | 0 | 0 | 0 | 0 | 114 |
| T120-1 | 1.00E−01 | 0 | 0 | 0 | 0 | 0 | | |
| T120-2 | 1.00E+00 | 0 | 0 | 0 | 0 | 0 | 0 | |
| T120-2 | 1.00E−01 | 0 | 0 | 0 | 0 | 0 | | |
| T120-3 | 1.00E+00 | 35 | 32 | 38 | 35 | 350 | 342 | |
| T120-3 | 1.00E−01 | 0 | 3 | 7 | 3 | 333 | | |

Conclusion

The results from this experiment are promising for both the Topas and the PMP samples. Both material samples saw near complete elimination of bacteria after 120 seconds of exposure. The data in this experiment, however, is noisy and has outliers. This experiment should be repeated in order verify that the UV lamp is able to disinfect through both materials. From our transmissivity tests, Topas should have better results but the data from this experiment does not show this. Future modifications to the experiment include reducing the exposure time, and ensuring that UV exposure and bacteria collection is consistent throughout the experiment.

Experiment 3

UV Mercury Lamp Experiment with Brand Cuvette Material and Topas

Abstract

The purpose of this experiment was to determine the antimicrobial effectiveness of an off-the-shelf UV lamp through multiple layers of UV transmissive polymers. Topas 8007X10 and Brand UV-cuvette samples were obtained and cut into small rectangular pieces of similar shape and size. *S. Aureus* liquid culture (1 uL) sitting beneath three layers of material was exposed to a Spectronics DeGERM-inator UV 5D lamp for 60 seconds or 120 seconds. A log 1 reduction of microorganisms was seen after 60 seconds of UV exposure. After 120 seconds, a log 3.3 reduction was seen for Topas while no colonies existed for the Brand UV-cuvette material.

Protocol

1. Biosafety:
   Spray the Biological Safety Cabinet (BSC) with 70% ethanol and wipe with kimwipe before and after the experiment. Also spray everything that goes in and out of the hood with 70% ethanol.
2. Pre-Experiment Methods:
   At least 24 hours before starting an experiment, two inoculum samples with the same organism but with different volumes will be prepared (24 hours for bacteria, 48 hours for fungi). One will have a total volume of 5 mL, and this will be used throughout the experiment the next day. The other will have a total volume of 1 mL, which will be used to increase the OD of the sample if needed.
   2.1. Obtain a stock plate of the organism and the appropriate media from the 6° C. refrigerator.
   2.2. Pour about 6 mL of media into a sterile 14 mL polypropylene tube with dual-position cap.
   2.3. Using a P1000, pipette 1 mL of media from the polypropylene tube into a sterile microcentrifuge.
   2.4. Using a sterile 1 uL disposable loop, swab several colonies from the stock plate and swirl the loop into the microcentrifuge. Place the loop into the waste beaker with 10% bleach.
   2.5. Vortex the microcentrifuge for 30 seconds.
   2.6. Label with the organism name and date.
   2.7. Using a new sterile 1 uL disposable loop, swab several colonies from the same stock plate and swirl the loop into the polypropylene tube with media. Place the loop into the waste beaker with 10% bleach.
   2.8. Completely seal the tube by pushing down on the plastic cap until you hear a pop.
   2.9. Vortex the tube for 30 seconds.
   2.10. Label the tube with the organism name and date.
   2.11. For bacteria, loosen the plastic cap and together with the microcentrifuge tube, place on the shaker inside the 37 C incubator. For yeast (*C. albicans*), loosen the plastic cap and allow to incubate at 25 C for 48 hours. For molds (*A. niger*), completely seal the tube by pushing down on the plastic cap and allow to incubate at 25 C for 48 hours.
3. Material Preparation
   3.1. Using a dremel with a cutting tip, cut four small rectangular pieces from the Topas 8007X10 sheet.
   3.2. Using a dremel with a cutting tip, cut and remove four faces of a Brand UV-cuvette macro.
   3.3. Place all the pieces into a beaker filled with 70% ethanol. Let sit for at least 1 minute.
   3.4. Dry the materials with kimwipes.
   3.5. Before using, make sure that that all surfaces are dry.
4. Control and Experimental Conditions
   4.1. For each control condition, inoculate 1 uL of liquid culture onto the center of a piece of sample material. Align and place another piece of material on top, sandwiching the liquid culture between the two pieces. Let sit for 5 minutes.
   4.2. For each experimental condition, inoculate 1 uL of liquid culture onto the center of a piece of sample material. Align and place another piece of material on top, sandwiching the liquid culture between the two pieces. Let sit for 5 minutes. After 5 minutes, place two additional pieces of material on top of the inoculated pieces. Center UV lamp directly over the setup and approximately 2.4 inches away from the inoculation point. Expose for 60 seconds or 120 seconds.

4.3. Collect from all samples.
5. Collection
  5.1. Using forceps which have been disinfected with 70% alcohol, remove the top two pieces of sample material (for the control condition, skip this step).
  5.2. Use the forceps to transfer the two pieces sandwiching the liquid culture into a pre-labeled 50 mL Falcon tube pre-filled with 9 mL of dialysate.
  5.3. Vortex Falcon tube for 2 minute.
  5.4. Transfer 1 mL of solution from the Falcon tube into the 10^0 well.
  5.5. Using the forceps, remove the sample material from the Falcon tube and drop into a 70% ethanol bath. Also place the two other pieces which were not touching the bacteria inside the ethanol bath.
6. Plating
  6.1 Label and pre-fill an autoclaved 96-well plate with 900 uL 0.85% saline.
  6.2 Vortex collected solution for 30 seconds then pipette 100 uL inoculum into the 10^-1 dilution well.
  6.3. With a new pipette tip, homogenize the solution by mixing thoroughly. Do this by pipetting the liquid up and down the well.
  6.4. Pipette 100 uL from the 10^-1 to the following well. Do this until desired dilution is reached. Do not forget to switch pipette tips before homogenizing the solution in each well.
  6.5. Pipette 100 uL from the dilutions into agar plates, then spread using a plastic spreader. Perform this three times on three separate agar plates, for each dilution. Label each plate appropriately (e.g. C1, 10^-1, A). For the 10^0 samples, make sure to vortex the falcon tube before pipetting onto the agar plates.
  6.6. Incubate the plated cultures (37 C for bacteria, room temperature for yeast and fungi) and monitor the growth on the plated cultures. The incubation time for bacteria is usually 16 hours, while for yeast and mold the incubation time is ~48 hours.
  6.7. Record time placed in incubator
  6.8. Record time taken out of the incubator
7. Clean-Up
  7.1. Place the material pieces into an ethanol bath.
  7.2 Soak plastic spreaders with 10% bleach, then ethanol and dry with kim wipes.
  7.3 Spray equipment with 70% ethanol.
  7.4 Make new plates, media, bleach, ethanol if necessary.
8. Bacterial Colony Formation Data Collecting
  8.1. Refer to the ATCC Product information sheet for specifics on the description of each colony. In general, colonies are entire, circular, and raised.
  8.2. Recognize the difference between two or more colonies that have grown into contact with each other.
  8.3. Have a second person check your count.
9. Data Analysis
  9.1. To calculate the bacterial cell count, divide the colony count by the dilution factor and the plated volume. The resulting units should be CFU/mL.
  9.2. Calculate the average bacterial cell count across the three plates of the same sample for each dilution factor.
  9.3. Calculate the average bacterial cell count of the same sample across dilution factors.
  9.4. Calculate the average total bacterial cell count across the control samples. This is the estimated total bacterial cell count of the original culture.

Results

| Summary Table | Brand Cuvette Control | Brand Cuvette - 60 s | Brand Cuvette - 120 s |
|---|---|---|---|
| Mean CFU/mL | 9478 | 382 | 0 |
| Kill Rate | | 95.97% | 100.00% |
| Log Reduction | | 1.39 | |

| Summary Table | Topas 8007X10 Control | Topas 8007X10 - 60 s | Topas 8007X10 - 120 s |
|---|---|---|---|
| Mean CFU/mL | 12106 | 1113 | 6 |
| Kill Rate | | 90.81% | 99.95% |
| Log Reduction | | 1.04 | 3.30 |

| Sample | Dilution | A | B | C | Mean | CFU/mL (across plates) | CFU/mL (across dilutions) | CFU/mL (across samples) |
|---|---|---|---|---|---|---|---|---|
| IC | 1.00E−01 | 93 | 87 | 99 | 93 | 9300 | 8650 | 10328 |
| IC | 1.00E−02 | 4 | 4 | 16 | 8 | 8000 | | |
| PC1 | 1.00E−01 | 39 | 70 | 57 | 55 | 5533 | 6100 | 9478 |
| PC1 | 1.00E−02 | 7 | 9 | 4 | 7 | 6667 | | |
| PC2 | 1.00E−01 | 61 | 67 | 51 | 60 | 5967 | 7650 | |
| PC2 | 1.00E−02 | 10 | 4 | 14 | 9 | 9333 | | |
| PC3 | 1.00E−01 | 156 | 160 | 115 | 144 | 14367 | 14683 | |
| PC3 | 1.00E−02 | 15 | 11 | 19 | 15 | 15000 | | |
| P60-1 | 1.00E+00 | 6 | 4 | 2 | 4 | 40 | 20 | 382 |
| P60-1 | 1.00E−01 | 0 | 0 | 0 | 0 | 0 | | |
| P60-2 | 1.00E+00 | 30 | 52 | 83 | 55 | 550 | 508 | |
| P60-2 | 1.00E−01 | 5 | 7 | 2 | 5 | 467 | | |
| P60-3 | 1.00E+00 | 57 | 75 | 69 | 67 | 670 | 618 | |
| P60-3 | 1.00E−01 | 9 | 4 | 4 | 6 | 567 | | |
| P120-1 | 1.00E+00 | 0 | 0 | 0 | 0 | 0 | 0 | 0 |
| P120-1 | 1.00E−01 | 0 | 0 | 0 | 0 | 0 | | |
| P120-2 | 1.00E+00 | 0 | 0 | 0 | 0 | 0 | 0 | |
| P120-2 | 1.00E−01 | 0 | 0 | 0 | 0 | 0 | | |
| P120-3 | 1.00E+00 | 0 | 0 | 0 | 0 | 0 | 0 | |
| P120-3 | 1.00E−01 | 0 | 0 | 0 | 0 | 0 | | |
| TC1 | 1.00E−01 | 96 | 103 | 86 | 95 | 9500 | 9750 | 12106 |

-continued

| | | | | | | | | |
|---|---|---|---|---|---|---|---|---|
| TC1 | 1.00E−02 | 7 | 16 | 7 | 10 | 10000 | | |
| TC2 | 1.00E−01 | 137 | 110 | 93 | 113 | 11333 | 10167 | |
| TC2 | 1.00E−02 | 11 | 7 | 9 | 9 | 9000 | | |
| TC3 | 1.00E−01 | 186 | 137 | 121 | 148 | 14800 | 16400 | |
| TC3 | 1.00E−02 | 12 | 18 | 24 | 18 | 18000 | | |
| T60-1 | 1.00E+00 | 16 | 16 | 10 | 14 | 140 | 153 | 1113 |
| T60-1 | 1.00E−01 | 3 | 2 | 0 | 2 | 167 | | |
| T60-2 | 1.00E+00 | 94 | 71 | 53 | 73 | 727 | 663 | |
| T60-2 | 1.00E−01 | 7 | 0 | 11 | 6 | 600 | | |
| T60-3 | 1.00E+00 | 259 | 233 | 241 | 244 | 2443 | 2522 | |
| T60-3 | 1.00E−01 | 18 | 28 | 32 | 26 | 2600 | | |
| T120-1 | 1.00E+00 | 0 | 0 | 0 | 0 | 0 | 0 | 6 |
| T120-1 | 1.00E−01 | 0 | 0 | 0 | 0 | 0 | | |
| T120-2 | 1.00E+00 | 0 | 1 | 0 | 0 | 3 | 18 | |
| T120-2 | 1.00E−01 | 1 | 0 | 0 | 0 | 33 | | |
| T120-3 | 1.00E+00 | 0 | 0 | 0 | 0 | 0 | 0 | |
| T120-3 | 1.00E−01 | 0 | 0 | 0 | 0 | 0 | | |

Conclusion

The results of this experiment were promising for both Topas 8007X10 and the Brand UV cuvette material. With 1 minute of exposure, we were able to achieve a log 1 reduction of *S. Aureus* for both materials. With 2 minutes of exposure, there was a 3.3 log reduction for Topas and complete elimination for the cuvette material. It is important to note that the bacteria count for the controls were very low in this experiment, thus the presence of a couple of colonies would significantly affect the log reduction. For each of the materials, the total thickness which the UV light had to travel through was 3.6 mm. Since we are stacking multiple layers of material on top of each other, there is also a small air gap in between the materials which will affect the refraction of light. We should expect better results if we are planning to use a thinner sample that consists of a single layer.

Experiment 4

UV Mercury Lamp Experiment with Quartz Tubes

Abstract

The purpose of this experiment was to determine the antimicrobial effectiveness of an off-the-shelf UV lamp on multiple layers of quartz tubes. For this experiment, the lumen of a 4 mm OD quartz tube (2 mm ID) was inoculated with 1 uL of *S. Aureus* liquid culture. The 4 mm OD tube was placed inside of a 6 mm OD quartz tube, which was then subsequently placed into a 10 mm OD quartz tube. The setup was directly exposed to a Spectronics DeGERM-inator UV 5D lamp for 10 seconds and for 30 seconds. Our results indicate that we were able to achieve a log 1 reduction of *S. Aureus* in 10 seconds, and over a log 3 reduction in 30 seconds. These results suggest that a quartz transfer set can be sterilized in 30 seconds.

1. Biosafety:
   Spray the Biological Safety Cabinet (BSC) with 70% ethanol and wipe with kimwipe before and after the experiment. Also spray everything that goes in and out of the hood with 70% ethanol.
2. Pre-Experiment Methods:
   At least 24 hours before starting an experiment, two inoculum samples with the same organism but with different volumes will be prepared (24 hours for bacteria, 48 hours for fungi). One will have a total volume of 5 mL, and this will be used throughout the experiment the next day. The other will have a total volume of 1 mL, which will be used to increase the OD of the sample if needed.
   2.1. Obtain a stock plate of the organism and the appropriate media from the 6° C. refrigerator.
   2.2. Pour about 6 mL of media into a sterile 14 mL polypropylene tube with dual-position cap.
   2.3. Using a P1000, pipette 1 mL of media from the polypropylene tube into a sterile microcentrifuge.
   2.4. Using a sterile 1 uL disposable loop, swab several colonies from the stock plate and swirl the loop into the microcentrifuge. Place the loop into the waste beaker with 10% bleach.
   2.5. Vortex the microcentrifuge for 30 seconds.
   2.6. Label with the organism name and date.
   2.7. Using a new sterile 1 uL disposable loop, swab several colonies from the same stock plate and swirl the loop into the polypropylene tube with media. Place the loop into the waste beaker with 10% bleach.
   2.8. Completely seal the tube by pushing down on the plastic cap until you hear a pop.
   2.9. Vortex the tube for 30 seconds.
   2.10. Label the tube with the organism name and date.
   2.11. For bacteria, loosen the plastic cap and together with the microcentrifuge tube, place on the shaker inside the 37 C incubator. For yeast (*C. albicans*), loosen the plastic cap and allow to incubate at 25 C for 48 hours. For molds (*A. niger*), completely seal the tube by pushing down on the plastic cap and allow to incubate at 25 C for 48 hours.
3. Prototype and Y-Set Preparation
   3.1. Place the quartz tubes and aluminum sheath into a beaker filled with 70% ethanol.
   3.2. Using a syringe, flush the lumens with 70% ethanol three times, air flushing in between.
   3.3. Dry the quartz tubes and aluminum sheath with kimwipes and sterilized cotton swabs.
   3.4. Before using, make sure that that all surfaces are dry.
4. Control and Experimental Conditions
   4.1. For each control condition, inoculate 1 uL of liquid culture in the lumen of the 4 mm OD quartz tube. Place the tube on its side and air dry for 5 minutes.
   4.2. For each experimental condition, first insert the long 4 mm OD quartz tube into the aluminum sheath. Place the 6 mm OD quartz tube over it. Inoculate the lumen of the 4 mm tube with 1 uL of liquid culture, then place the 10 mm OD quartz tube over the smaller tubes. Let the setup sit and air dry for 5 minutes. Position the UV lamp directly over the setup, resting each side of the lamp on 4 Petri dishes. In one condition, turn the UV lamp on for 10 seconds. In the other condition, turn the UV lamp on for 30 seconds.
4.3 Collect from all samples.
5. Collection
5.1. Carefully remove the tubes from the aluminum sheath.
5.2 Place the 6 mm OD and 10 mm OD tubes into an ethanol bath.
5.3 Using a syringe, flush the lumen of the 4 mm tube on the opposite side from which it was inoculated, with 9 mL of dialysate into a pre-labeled Falcon tube.
5.4. Air flush the lumen of the 4 mm OD tube three times to remove any remaining liquid.
5.5. Place the 4 mm OD tube into the ethanol bath.
6. Plating
6.1. Label and pre-fill an autoclaved 96-well plate with 900 uL 0.85% saline.
6.2. Vortex collected solution for 30 seconds then pipette 100 uL inoculum into the 10^-1 dilution well.
6.3. With a new pipette tip, homogenize the solution by mixing thoroughly. Do this by pipetting the liquid up and down the well.
6.4. Pipette 100 uL from the 10^-1 to the following well. Do this until desired dilution is reached. Do not forget to switch pipette tips before homogenizing the solution in each well.
6.5 Pipette 100 uL from the dilutions into agar plates, then spread using a plastic spreader. Perform this three times on three separate agar plates, for each dilution. Label each plate appropriately (e.g. C1, 10^-1, A). For the 10^0 samples, make sure to vortex the falcon tube before pipetting onto the agar plates.
6.6. Incubate the plated cultures (37 C for bacteria, room temperature for yeast and fungi) and monitor the growth on the plated cultures. The incubation time for bacteria is usually 16 hours, while for yeast and mold the incubation time is ~48 hours.
6.7. Record time placed in incubator
6.8. Record time taken out of the incubator
7. Clean-Up
7.1. Place the quartz tubes and aluminum sheath into an ethanol bath.
7.2. Soak plastic spreaders with 10% bleach, then ethanol and dry with kim wipes.
7.3. Spray equipment with 70% ethanol.
7.4. Make new plates, media, bleach, ethanol if necessary.
8. Bacterial Colony Formation Data Collecting
8.1. Refer to the ATCC Product information sheet for specifics on the description of each colony. In general, colonies are entire, circular, and raised.
8.2. Recognize the difference between two or more colonies that have grown into contact with each other.
8.3. Have a second person check your count.
9. Data Analysis
9.1. To calculate the bacterial cell count, divide the colony count by the dilution factor and the plated volume. The resulting units should be CFU/mL.
9.2. Calculate the average bacterial cell count across the three plates of the same sample for each dilution factor.
9.3. Calculate the average bacterial cell count of the same sample across dilution factors.
9.4. Calculate the average total bacterial cell count across the control samples. This is the estimated total bacterial cell count of the original culture.

Results

| Summary Table | Control | 10 seconds | 30 seconds |
|---|---|---|---|
| With Outliers | | | |
| Mean CFU/mL | 21542 | 1213 | 6 |
| Kill Rate | | 94.37% | 99.97% |
| Log Reduction | | 1.25 | 3.59 |
| Without Outliers | | | |
| Mean CFU/mL | 15621 | 1213 | 6 |
| Kill Rate | | 92.24% | 99.96% |
| Log Reduction | | 1.11 | 3.45 |

| Sample | Dilution | A | B | C | Mean | CFU/mL (across plates) | CFU/mL (across dilutions) | CFU/mL (across samples) |
|---|---|---|---|---|---|---|---|---|
| IC | 1.00E−01 | 442 | 440 | 428 | 437 | 43667 | 50000 | 50000 |
| IC | 1.00E−02 | 64 | 43 | 62 | 56 | 56333 | | |
| C1 | 1.00E−01 | 151 | SMEAR | 130 | 141 | 14050 | 18025 | 21542 |
| C1 | 1.00E−02 | 25 | 19 | SMEAR | 22 | 22000 | | |
| C2 | 1.00E−01 | 272 | 218 | 303 | 264 | 26433 | 33383 | |
| C2 | 1.00E−02 | 23 | 41 | 57 | 40 | 40333 | | |
| C3 | 1.00E−01 | 143 | 126 | 124 | 131 | 13100 | 13217 | |
| C3 | 1.00E−02 | 23 | 4 | 13 | 13 | 13333 | | |
| E10-1 | 1.00E+00 | 109 | SMEAR | 97 | 103 | 1030 | 1198 | 1213 |
| E10-1 | 1.00E−01 | 14 | 12 | 15 | 14 | 1367 | | |
| E10-2 | 1.00E+00 | SMEAR | 155 | 152 | 154 | 1535 | 1734 | |
| E10-2 | 1.00E−01 | 16 | 15 | 27 | 19 | 1933 | | |
| E10-3 | 1.00E+00 | 67 | 38 | 63 | 56 | 560 | 705 | |
| E10-3 | 1.00E−01 | 14 | SMEAR | 3 | 9 | 850 | | |
| E30-1 | 1.00E+00 | 0 | 0 | 0 | 0 | 0 | 0 | 6 |
| E30-1 | 1.00E−01 | 0 | 0 | 0 | 0 | 0 | | |
| E30-2 | 1.00E+00 | 0 | 0 | 0 | 0 | 0 | 17 | |
| E30-2 | 1.00E−01 | 1 | 0 | 0 | 0 | 33 | | |
| E30-3 | 1.00E+00 | 0 | 0 | 0 | 0 | 0 | 0 | |
| E30-3 | 1.00E−01 | 0 | 0 | 0 | 0 | 0 | | |

Conclusion

In this experiment, we were able to achieve a good kill rate on the quartz tubes with 30 seconds of sterilization time. While the inoculation control (IC) revealed that we were not effectively collecting all of the bacteria, the results were mostly consistent across samples. In this experiment, the UV source was placed approximately two inches away from the inoculation point. It is possible that this distance will be smaller in a commercial device, thus decreasing the amount of sterilization time needed. There are many variations in this experiment, since no consistent fixtures were used. Overall, the results suggest that UV light is able to effectively disinfect through multiple layers of quartz.

METHOD OF USE

The fluid from the dialysate bag 18 (FIG. 1) is delivered into the peritoneal cavity (the abdominal body cavity around the intestine), where the peritoneal membrane acts as a semipermeable membrane. The peritoneal membrane or peritoneum is layer of tissue containing blood vessels that lines the peritoneal, or abdominal, cavity and the internal abdominal organs (including the stomach, spleen, liver, and intestines). The dialysate is left there for a period of time to absorb waste products from the patient 22, and then it is drained out through the implanted tube 12. This cycle or "exchange" may be repeated 4-5 times (or more often with an automated system) per day.

Although particular embodiments have been shown and described, it will be understood that they are not intended to limit the claimed inventions, and it will be obvious to those skilled in the art that various changes and modification may be made without departing from the spirit and scope of the claimed inventions. The specification and drawings are, accordingly, to be regarded in an illustrative rather than restrictive sense. The claimed inventions are intended to cover alternatives, modifications, and equivalents.

What is claimed:

1. An assembly for disinfecting a connection, comprising;
    a connection comprising a first connector and a second connector;
    a housing having an inner surface, an outer surface, a hinged cover to removably contain the connection, a first aperture within a first wall of the housing sized to receive the first connector, and a second aperture within a second wall of the housing sized to receive the second connector, the first aperture having a size different from the size of the second aperture;
    an UV light source mounted inside the housing so that no portion of the UV light source contacts the housing inner surface; and
    a power source and an electronic circuit for controlling electrical power to the UV light source;
    wherein the first and second apertures are arranged within the housing to properly position the first connector and the second connector to receive UV light.

2. The assembly of claim 1, wherein the housing has a first chamber and a second chamber, the UV light source being mounted in the first chamber and the power source being mounted in the second chamber.

3. The assembly of claim 1, wherein the first connector includes a transfer set connector and the second connector includes a Y-set connector.

4. The assembly of claim 3, wherein the connectors are formed of a material that is transmissive of UV light.

5. The assembly of claim 4, wherein the transfer set connector and the Y-set connector are formed from a transmissive polymer.

6. The assembly of claim 1, wherein in the UV light source is ultraviolet C and has a wavelength in the range of 100 nm to 280 nm.

7. The assembly of claim 6, wherein the UV light includes any of a mercury lamp, light emitting diode, or fluorescent lamp.

8. The assembly of claim 1, wherein the housing comprises an elliptical shape and has a first foci $F_1$ and a second foci $F_2$, the UV light source being mounted at the first foci $F_1$, and the connection being mounted at the second foci $F_2$.

9. An assembly for disinfecting a connection, comprising;
    a connection comprising a first connector and a second connector;
    a housing having an inner surface, an outer surface, a cover, a first aperture within a first wall of the housing sized to receive the first connector, and a second aperture within a second wall of the housing sized to receive the second connector, the first aperture having a size different from the size of the second aperture;
    an UV light source mounted in a first region; and
    a power source and an electronic circuit for controlling electrical power to the UV light source mounted outside the first region,
    wherein the first and second apertures are arranged within the housing to properly position the first connector and the second connector to receive UV light.

10. A method for disinfecting a connection, comprising;
    providing the connection comprising a first connector and a second connector;
    providing a housing having an inner surface, an outer surface, a cover to removably contain the connection, a UV light source, a first aperture within a first wall of the housing sized to receive the first connector, and a second aperture within a second wall of the housing sized to receive the second connector, the first aperture having a size different from the size of the second aperture; and
    removably inserting the connection such that the first connector is positioned in the first aperture and the second connector is positioned in the second aperture, thereby properly positioning the connection for receiving UV light.

* * * * *